United States Patent
Maltezos et al.

(10) Patent No.: US 9,212,994 B2
(45) Date of Patent: *Dec. 15, 2015

(54) FLUORESCENCE DETECTOR, FILTER DEVICE AND RELATED METHODS

(75) Inventors: George Maltezos, Fort Salonga, NY (US); John Kim Lee, New York, NY (US); Axel Scherer, Laguna Beach, CA (US); Emil Kartalov, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1009 days.

This patent is subject to a terminal disclaimer.

(21) Appl. No.: 13/348,495

(22) Filed: Jan. 11, 2012

(65) Prior Publication Data

US 2012/0141337 A1 Jun. 7, 2012

Related U.S. Application Data

(63) Continuation of application No. 11/804,112, filed on May 17, 2007, now Pat. No. 8,137,626.

(60) Provisional application No. 60/802,068, filed on May 19, 2006, provisional application No. 60/900,426, filed on Feb. 9, 2007.

(51) Int. Cl.
*B01D 35/00* (2006.01)
*G01N 21/64* (2006.01)

(52) U.S. Cl.
CPC ........ *G01N 21/6456* (2013.01); *G01N 21/6452* (2013.01); *Y10T 137/2224* (2015.04)

(58) Field of Classification Search
None
See application file for complete search history.

(56) References Cited

U.S. PATENT DOCUMENTS

| | | | |
|---|---|---|---|
| 6,302,134 B1 | 10/2001 | Kellogg et al. | |
| 6,326,211 B1 | 12/2001 | Anderson | |
| 6,512,236 B2 | 1/2003 | Seville | |
| 6,830,936 B2 | 12/2004 | Anderson | |
| 6,915,679 B2 | 7/2005 | Chien | |
| 7,221,455 B2 | 5/2007 | Chediak et al. | |
| 7,445,926 B2 | 11/2008 | Mathies | |
| 7,473,397 B2 | 1/2009 | Griffin et al. | |
| 7,854,897 B2 | 12/2010 | Tanaami et al. | |
| 8,137,626 B2 * | 3/2012 | Maltezos et al. | 422/82.07 |
| 8,182,765 B2 | 5/2012 | Hodges | |
| 8,187,541 B2 | 5/2012 | Maltezos et al. | |
| 8,703,457 B2 * | 4/2014 | Yasuda et al. | 435/173.9 |
| 2002/0144738 A1 | 10/2002 | Unger | |
| 2002/0159919 A1 | 10/2002 | Churchill | |
| 2003/0040119 A1 * | 2/2003 | Takayama et al. | 436/63 |
| 2003/0049833 A1 * | 3/2003 | Chen et al. | 435/287.2 |
| 2004/0086427 A1 | 5/2004 | Childers | |
| 2004/0254559 A1 | 12/2004 | Tanaami | |
| 2005/0026301 A1 | 2/2005 | Petithory | |
| 2005/0139547 A1 * | 6/2005 | Manoussakis et al. | 210/645 |
| 2006/0008913 A1 * | 1/2006 | Angelescu et al. | 436/28 |
| 2006/0068490 A1 | 3/2006 | Tang et al. | |
| 2006/0204699 A1 * | 9/2006 | Maltezos et al. | 428/36.91 |
| 2006/0222569 A1 | 10/2006 | Barten et al. | |
| 2006/0264779 A1 | 11/2006 | Kemp | |
| 2007/0178009 A1 * | 8/2007 | Sakaino et al. | 422/56 |
| 2007/0225922 A1 | 9/2007 | Foss et al. | |
| 2007/0275455 A1 | 11/2007 | Hung | |
| 2008/0025888 A1 | 1/2008 | Gotzen | |

OTHER PUBLICATIONS

Notice of Allowance issued for U.S. Appl. No. 11/856,722, filed Sep. 18, 2007 in the name of George Maltezos et al. mail date: Mar. 2, 2012.
Final Office Action issued for U.S. Appl. No. 11/856,722, filed Sep. 18, 2007 in the name of George Maltezos et al. mail date: Nov. 22, 2011.
Non-Final Office Action issued for U.S. Appl. No. 13/457,199, filed Apr. 26, 2012 in the name of George Maltezos et al. mail date: Aug. 16, 2012.
Final Office Action issued for U.S. Appl. No. 13/457,199, filed Apr. 26, 2012 in the name of George Maltezos et al. mail date: Feb. 7, 2013.
Non-Final Office Action issued for U.S. Appl. No. 13/457,199, filed Apr. 26, 2012 in the name of George Maltezos et al. mail date: Aug. 6, 2013.
Final Office Action issued for U.S. Appl. No. 13/457,199, filed Apr. 26, 2012 in the name of George Maltezos et al. mail date: Mar. 19, 2014.
Non-Final Office Action issued for U.S. Appl. No. 13/457,199, filed Apr. 26, 2012 in the name of George Maltezos et al. mail date: Jan. 20, 2015.

* cited by examiner

*Primary Examiner* — Ann Lam
(74) *Attorney, Agent, or Firm* — Steinfl & Bruno LLP

(57) ABSTRACT

A microfluidic filter is disclosed. The filter can be used with onchip fluid filtration such as whole blood filtration for microfluidic blood analysis. The filter is able to filter the necessary volume of fluid and in particular blood in an acceptable time frame.

17 Claims, 24 Drawing Sheets

| | | | | | | |
|---|---|---|---|---|---|---|
| Albumin | 3.5-7.5 g/dL | 7 | normal range | 4 hours | 68 | 5.50E+11 | 9.14E-04 |
| C3 complement | 70-150 mg/dL | 7 | normal range | 4 days | 174 | 3.80E+09 | 6.31E-06 |
| Ceruloplasmin | 21-50 mg/dL | 5 | normal range | 36 hours | 132 | 1.80E+09 | 2.98E-06 |
| beta2 Microglobulin | >2.0mg/L | 7 | is abnormal | 1 day | 11.8 | 1.00E+08 | 1.66E-07 |
| Thyroxine (T4) | 5-12 ug/dL | 7 | normal range | 72 hours | 777 | 6.60E+07 | 1.10E-07 |
| C-reactive protein | <1.2 mg/dL | 5 | is abnormal | 4 hours | 114 | 6.60E+07 | 1.10E-07 |
| Ferritin | 30-300 ng/mL | 7 | male range | 72 hours | 474 | 2.10E+05 | 3.49E-10 |
| AFP | >20 ng/mL | 7 | is abnormal | 96 hours | 70 | 1.70E+05 | 2.82E-10 |
| PSA | >4.0 ng/mL | 7 | is abnormal | 96 hours | 30 | 8.00E+04 | 1.33E-10 |
| VEGF | 2500 pg/mL | vary | plasma normal | days | 26 | 5.80E+04 | 9.63E-11 |
| Creatin Kinase MB | >5.0 ng/mL | 7 | indicates infarct | 4 hours | 84 | 3.60E+04 | 5.98E-11 |
| Thyroglobulin | 5-50 ng/mL | 5 | normal range | 7 days | 670 | 2.50E+04 | 4.15E-11 |
| CEA | >3.0 ng/mL | 7 | is abnormal | 72 hours | 180 | 1.00E+04 | 1.66E-11 |
| Calcitonin | >40 pg/mL | 5 | is abnormal | 4 days | 3,500 | 6.80E+03 | 1.13E-11 |
| Vasopressin | 2-12 pg/mL | 10 | plasma normal | 7 days | 1,064 | 3.30E+03 | 5.48E-12 |

FIG. 8

FLUORESCENCE DETECTOR, FILTER DEVICE AND RELATED METHODS

RELATED APPLICATIONS

This application is a U.S. continuation application of U.S. patent application Ser. No. 11/804,112 Filed May 17, 2007, which in turn claims the benefit of provisional application 60/802,068 for "Personalized Medicine Device" filed on May 19, 2006 and incorporated herein by reference in its entirety. U.S. patent application Ser. No. 11/804,112 also claims the benefit of provisional application 60/900,426 for "Microfluidic Device to Extract Blood Plasma from a Finger Stick" filed on Feb. 9, 2007, also incorporated herein by reference in its entirety. The present application is also related to U.S. patent application Ser. No. 11/439,288 "High Throughput Multi-Antigen Microfluidic Fluorescence Immunoassays" filed on May 22, 2006 and to U.S. patent application Ser. No. 11/297,651, "Prototyping Methods and Devices for Microfluidic Components", filed on Dec. 7, 2005 all of which are also incorporated herein by reference in their entirety.

GOVERNMENT INTEREST

The U.S. Government has certain rights in this invention pursuant to DARPA grant no. HR0011-04-1-0032, NIH grant no. HG022644, and NIH, grant no. HG002644.

BACKGROUND

1. Field

The present disclosure relates to the field of sample analysis, in particular to sample analysis performed for medical purpose. More in particular, the present disclosure relates to a sample filter suitable for separating sample components to be analyzed and to a fluorescence detector suitable for detecting fluorescence signal resulting from a fluorescence assay and related methods.

2. Related Art

In a fluorescence assay, the intensity of fluorescence is used to read the concentration of the antigen, and is typically measured with a fluorescence microscope or a laser scanner. The measured fluorescent intensity is typically compared to a previously measured "standard curve" made from previous measurements of standard samples in order to ascertain the concentration of antigen in the current sample. This serial measurement process is both time-consuming and expensive, and limits the speed with which a fluorescence assay can be completed.

Many approaches for fluorescence assay test chips have been attempted so far. Such approaches use glass, $TiO_2$, silicon, and silicone fluidics and have so far demonstrated the opportunities of more complex fluidic systems. In particular microfluidics technology provides the foundation for advances in this field. Soft-Lithography allows for the cheap and efficient creation of polymer chips able to perform Sandwich Enzyme-Linked ImmunoSorbent Assay (ELISA) tests on a microscopic scale. Such systems can run with a reduced amount of sample fluid, (e.g. less than a drop of patient blood serum) and synthesized proteins unlike the current macroscopic versions which require significant amounts of both.

By reducing the size of devices, cost of manufacturing, and amount of material needed these chips prove essential in the creation of point of care medical testing. However, until now, the read-out mechanism for such chips has involved the use of rather large fluorescence microscopes or laser scanners.

The use of large size and high cost equipment impacts in particular performance of fluorescence assays for medical purposes, in particular diagnostic assays. The high cost and time requirements for medical testing restrict prompt detection and efficient treatment of ailments. Modern medical technology remains large and expensive, requiring centralized healthcare systems which increase delays, price, and the probability of clerical error and often cause prolonged hospital stays.

Ideally, more compact handheld devices are desirable in particular for point of care diagnostic assays that can evaluate fluorescence from multiple chambers in parallel by using multi-element imaging detecting devices.

Microfluidic testing also requires the extraction and analysis of small quantities of patient's fluids. In particular, when the fluid is blood, working with on-chip microsystems for whole blood analysis, requires processing the whole blood into components that can be analyzed using microfluidic technology.

It is well known that cell inclusion may lead to cell lysis affecting the reproducibility and standardization of blood tests. It is also well known that removing blood cells in an initial step can be important since miniaturized downstream systems, such as on-chip detection modules, protein analysis, PCR etc are prone to be clogged by cells and coagulation. Blood filtration is necessary for all assays requiring plasma as well. Viral screening and other blood-type analysis may not deal specifically with blood cells, but what else may be found in blood—such as proteins or antibodies. In that context, it is necessary to filter whole blood.

In the context of microfluidic blood analysis, the system of blood filtration and anti-coagulation is necessary to handle blood samples in a miniaturized format. That is to say, there must be a way to separate blood cells and plasma from whole blood, on a microfluidic scale, for proper microfluidic blood analysis. Known filters in planar poly(dimethylsiloxane) (PDMS) require registration and sealing between two layers and the filter. This is difficult because only the thinnest of filters can be sealed this way, and leakage is a problem.

With the increased use of microfluidic technology in the fields of physics, chemistry, engineering, biotechnology, and especially medicine, it has become increasingly more important to discover more viable and more efficient system of blood filtration and anti-coagulation, a procedural practice for microscale whole blood analysis.

SUMMARY

According to a first aspect, an fluorescence assay detector is provided, comprising: an excitation filter; an emission filter; a microfluidic fluorescence assay apparatus located between the excitation filter and the emission filter, the microfluidic fluorescence assay apparatus comprising a fluorescence source; a light emitting device to excite the fluorescent source; a detecting arrangement for detecting fluorescence signals or images on the microfluidic fluorescence assay apparatus.

According to a second aspect, a method for detecting fluorescence assay signals is provided, comprising: providing excitation light at an excitation frequency to excite a fluorophore, allowing the fluorophore to emit light in connection with a microfluidic assay apparatus; filtering the excitation light; filtering light emitted through the fluorophore; and detecting fluorescence signals or images thus generated.

A first advantage of the detector and detecting method disclosed herein, is the possibility to perform fluorescence detection from microfluidic assay chips with digital imaging equipment reduced in size and able to obtain multiple assay readings in parallel.

A second advantage of detector and detecting method disclosed herein is the possibility to provide equipment to perform fluorescence identification of many proteins in many blood samples, the equipment reduced in size so that it is portable.

A third advantage of the detectors and detecting methods disclosed herein is that as a consequence of the reduction in size of the equipment a diagnostic tool resulting in improved cost, manufacturability and ease of operation can be constructed. The detector and detecting method could be particularly useful in multi-analyte high-throughput assay in several fields, including medical immunoassay tests.

According to a third aspect, a microfluidic filter forming mold is provided, comprising: a top pin; a bottom pin connected with the top pin but separable from the top pin, the bottom pin including an internal pin; a top piece with which the top pin is connected; and a bottom piece with which the bottom pin is connected. The mold can further comprise the microfluidic filter, which in a preferred embodiment is a blood filter.

According to a fourth aspect, a three-dimensional polymeric structure comprising a polymeric cast of the above mold is provided. The three-dimensional polymeric structure can include a microfluidic filter.

The three-dimensional polymeric structure and of the single piece polymeric structure of microfluidic filter device, can also be integrated with microfluidic channeling structures associated to an inputting end and/or an outputting end of the structure. The microfluidic channeling structure on the outputting end is adapted to interface with a microfluidic assay apparatus. The fluid would pass from the inputting end to the outputting end of the structure through the filter embedded in the three-dimensional polymeric structure, separating the fluid component which would be used in the microfluidic assay apparatus.

According to a fifth aspect a microfluidic filtering device is disclosed, the device comprising a microfluidic filter cast in a single piece polymeric structure, the microfluidic filter connected to an inputting end of the structure through a microfluidic inputting channel, the microfluidic filter connected to an outputting end of the polymeric piece structure through an outputting microfluidic channel.

The microfluidic filtering device, can also be integrated with microfluidic channeling structures associated to the inputting end and/or the outputting end of the structure according to what described for the three dimensional polymeric structure, mutatis mutandis.

According to a sixth aspect, a process for fabricating a three-dimensional fluid filtering device, in particular a blood filtering device, structure is provided, the process comprising: providing a mold having a top pin, a bottom pin and a blood filter between the top pin and the bottom pin; pouring polymer on the mold; curing the polymer; separating the top pin from the bottom pin to free the blood filter; and extracting the mold from the polymer while leaving the blood filter in the polymer.

An advantage of the filtering structures and devices in accordance with the present disclosure over traditional planar microfluidics for filtration in that a leak tight seal can be formed by virtue of the fact that the entire device is in one piece of polymer.

According to a seventh aspect a microfluidic filtering and detecting assembly, is disclosed, the assembly comprising: the three-dimensional structure or the microfluidic filtering device herein described; and the fluorescence assay detector of claim herein described.

According to a eight aspect a portable diagnostic system/ assembly is disclosed, the system comprising: a sample preparation stage: and a sample analysis stage to detect analytes.

In the portable diagnostic system herein disclosed the sample preparation stage can comprise a microfluidic circuit with a fluorescent fluid source, and the sample analysis stage can comprise: an excitation filter; an emission filter; a light emitting device to excite the fluorescent fluid source; and a detecting arrangement for detecting fluorescence images from the microfluidic circuit, with the microfluidic circuit located between the excitation filter and the emission filter. The detecting arrangement can also include means for comparing the fluorescence images detected to predetermined standard images to provide a qualitative or a quantitative diagnostic indication.

BRIEF DESCRIPTION OF THE DRAWINGS

FIG. 8 shows cancer markers and their clinically relevant concentrations within human blood.

DETAILED DESCRIPTION

According to a first embodiment a microfluidic fluorescence assay detector and related methods are disclosed, the detectors to be used in combination with a microfluidic fluorescence assay apparatus, circuit or chip. In certain embodiments, the microfluidic fluorescence chip is a high-throughput multi-antigen fluorescence microfluidic assay chip, such as immunoassay-chips made from PDMS or other polymers such as SIFEL® (a fluorocarbon siloxane rubber precursor by Shin Etsu Chemical Co., Ltd), which can provide quantitative blood analysis at clinically relevant levels, such as 10-100 pM.

In Applicants' most recently developed immunoassay chips, active microfluidic matrix formats utilize arrays of integrated micromechanical valves to direct pressure-driven flow and to multiplex analyte samples with immunoassay reagents. ELISA-like fluorescence immunostacks are formed in the microchambers at the intersections of sample and reagent channels. In the present disclosure, Applicants show that the fluorescence signals of the captured antigens from these microchambers can be measured with a digital camera or photodetector.

Although the following detailed description makes often reference to immunoassays chips, the detector and detection system of the present disclosure, can also be used in connection with microfluidic chips adapted to perform DNA hybridization assays such as the ones performed in standard DNA microarrays, expression analysis of mRNA, certain forms of DNA detection and/or DNA sequencing (see e.g. Kartalov, Emil P. and Quake, Stephen R. (2004) Microfluidic device reads up to four consecutive base pairs in DNA sequencing-by-synthesis in Nucleic Acids Research, 32 (9). pp. 2873-2879 herein incorporated by reference in its entirety).

In any of those embodiments, the test matrix can be expanded to measure a significantly large numbers of samples by exploiting the capabilities of microfluidic technology, resulting in even greater advantages of parallel fluorescence measurement.

Figure 1:
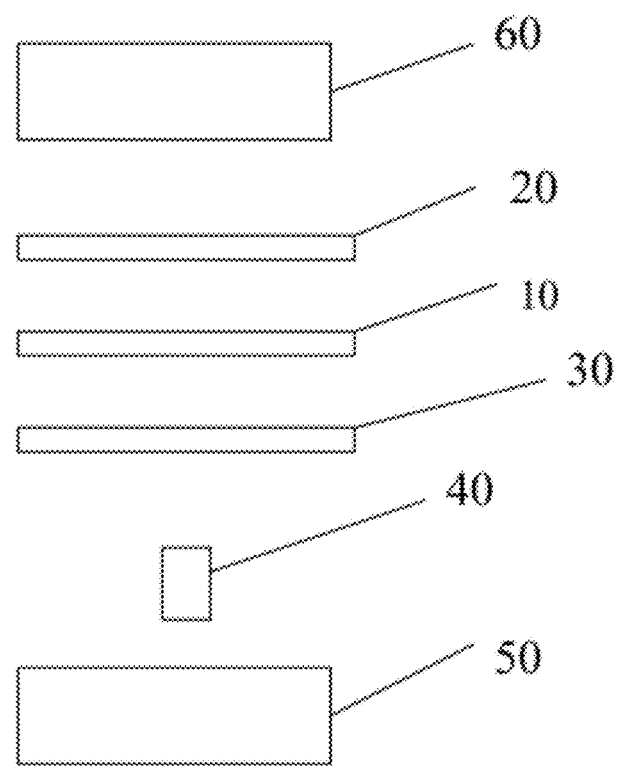
FIG. 1 shows a schematic representation of the device according to the present disclosure.

FIG. 1 shows a schematic representation of the device according to the present disclosure. A microfluidic circuit or chip 10 is located between an excitation filter 20 and an emission filter 30. The output image of the microfluidic chip 10 is detected by a combination of a lens 40 and a camera 50. In particular, lens 40 and camera or detector 50 will allow a digital image of microfluidic chip 10 to be obtained. The camera or detector 50 can be, for example, a Canon EOS digital "Rebel" camera, a photodiode, phototransistor or other detector. In order to excite the fluorescence source of the microfluidic chip 10, a light-emitting device 60 is provided. The light-emitting device 60 can be a light emitting diode (LED) or a mercury lamp or laser.

Figure 6:
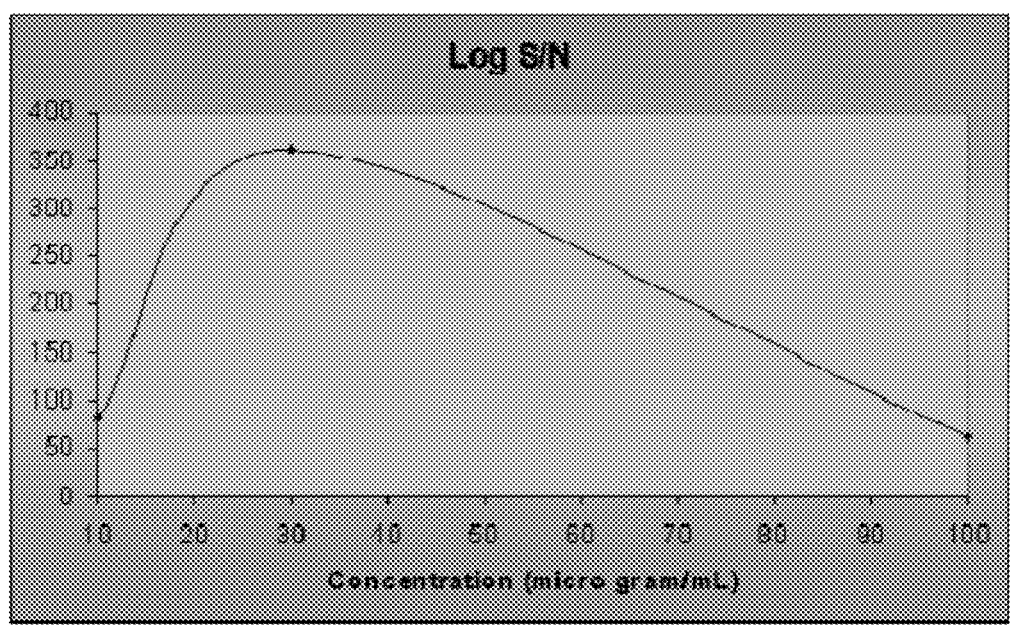
Figure 7:
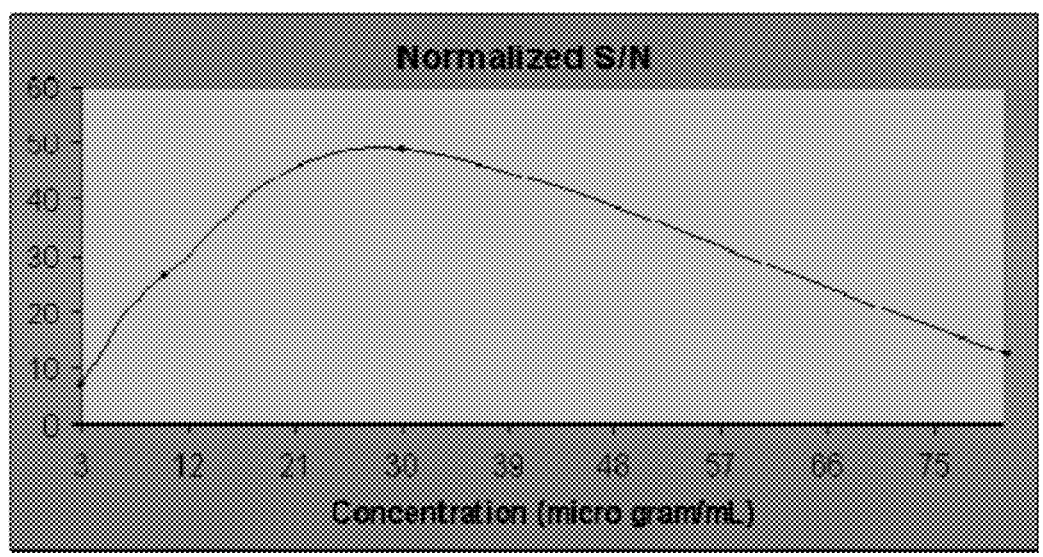

In an alternative embodiment, the excitation light source and detector can be placed at right angles to one another in a configuration that uses a dichroic mirror in the standard configuration to increase background filtering and a Signal to Noise Ratio (SNR) (with reference to use of SNR in the detector herein disclosed see below description of FIGS. 5 to 7).

In certain embodiments, the detector of the present disclosure can include optical fibers, or bundles thereof, to deliver the excitation and emission light to and from specific locations on the chip, to particular pixels or clusters of pixels on the detector. In particular, in those embodiments, the lenses in the detector can be replaced by the optical fibers and the detector can include a CCD imager, a CMOS imager, an Avalanche Photodiodes (APD) array etc.

Figure 2:
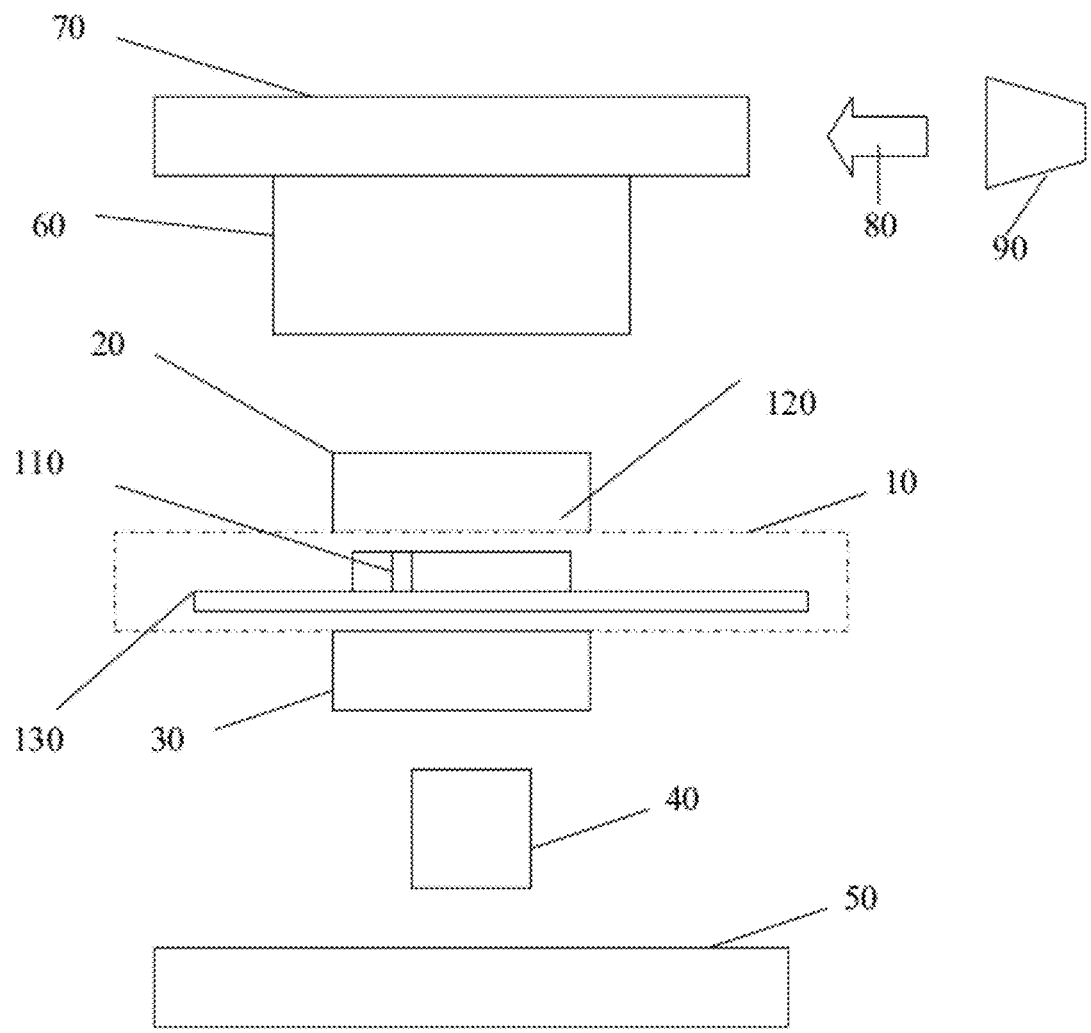
FIG. 2 shows a more detailed representation of the arrangement of FIG. 1.

FIG. 2 shows a more detailed representation of the arrangement of FIG. 1. In particular, the microfluidic circuit 10 includes a fluorescence source 110 (e.g., the fluorophore Alexa Fluor 555 solution in a concentration ranging, for example, from 0.01 g/ml to 300 g/ml in water) associated with a microfluidic structure 120, both of which are on top of a glass piece 130. In some embodiments the microfluidic chip 10 can be of the type shown in U.S. Ser. No. 11/439,288 "High Throughput Multi-Antigen Microfluidic Fluorescence Immunoassays" filed on May 22, 2006 and incorporated herein by reference in its entirety. Further microfluidic chips, including but not limited to chips made of elastomers or polymers such as PDMS, PMMA, Polyurethane, PFPE, SIFEL®, parylene, and others, can be used in combination with a detector of the present disclosure. In some embodiments those chips are adapted to perform DNA hybridization assays, expression analysis of mRNA, certain forms of DNA detection and/or DNA sequencing. Those chips are identifiable by a skilled person upon reading of the present disclosure and will not be further discussed here in details.

The light emitting device 60 is connected to a heat sink 70 which, in turn, receives cool air 80 from a fan 90. Both the light emitting device 60 and the fan 90 are connected to power sources, not shown in the figure. Although the heat sink 70 is optional, it is advantageous when high power LED's are used as light emitting devices 60. In such embodiments, the heat sink 60 gives better longevity and—more importantly—stability of the LED wavelength.

Figure 3:
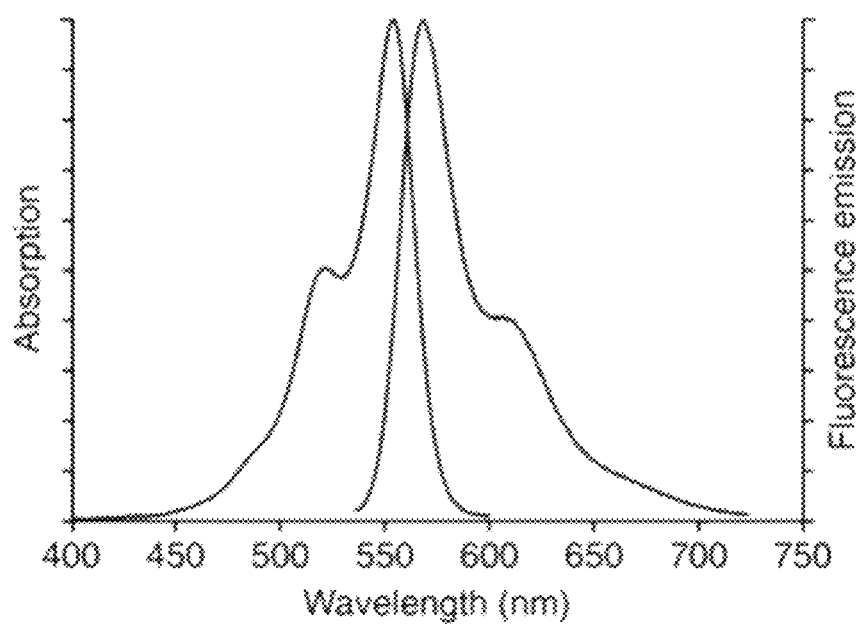
FIG. 3 shows a graph illustrating The emission and excitation curves of Alexafluor 555 spinner from Laurel Technologies Corp.

When combined with a LED source 60, the digital camera or detector 50 provides a compact portable fluorescence imaging system, as two 6V lantern batteries connected in series can be used to power the electronics. The excitation filter 20 serves to protect the camera 50 and can be, for example, HQ 545/25 by Chroma. The LED, laser diode or mercury light source 60 can be selected to emit at a wavelength of approximately 545 nm. A graph showing the emission and excitation curve of the exemplary fluorophores Alexa Fluor 555 is shown in FIG. 3.

In the following paragraphs preceding the discussion of FIG. 4A and FIG. 4B, an exemplary technique for obtaining an exemplary circuit 10 suitable to be used in combination with the detector of the present disclosure, will be explained.

PDMS microfluidic chips with integrated micromechanical valves were built using soft lithography as described, for example, in "Monolithic Microfabricated Valves and Pumps by Multilayer Soft Lithography", by Marc A. Unger, Hou-Pu Chou, Todd Thorsen, Axel Scherer, Stephen R. Quake, Science 7 April 2000, Vol. 288. no. 5463, pp. 113-116, and "High-throughput multi-antigen microfluidic fluorescence immunoassays by Emil P. Kartalov, Jiang F. Zhong, Axel Scherer, Stephen R. Quake, Clive R. Taylor, and W. French Anderson in Biotechniques 2006 Volume 40, Number 1: pp 85-90, both incorporated herein by reference in their entirety, with the following modifications.

Silicon wafers were exposed to HMDS vapor for 3 min. Photoresist SPR 220-7 was spun at 2,000 rpm for 60 sec on a Model WS-400A-6NPP/LITE spinner from Laurel Technologies Corp. The wafers were baked at 105 deg C. for 90 sec on a hotplate. UV exposure through black-and-white transparency masks was performed for 1.75 min on a mask aligner (Karl Suss America Inc., Waterbury, Vt.). The molds were then developed for 2 min in 100% 319 MicroChem developer. Flow layer molds were baked at 140 deg C. for 15 min on a hotplate to melt and round the flow channels. Molds were characterized on an Alpha-Step 500 (KLA-Tencor, Mountain View, Calif. 94043). Channel height was between 9 and 10 µm. Control channel profile was oblong, while flow channel profile was parabolic. Except for the height measurements, the mold fabrication was conducted in a class-10,000 clean room.

Molds were exposed to TMCS vapor for 3 min. PDMS in 5:1 and 20:1 ratios were mixed and degassed using an HM-501 hybrid mixer and cups from Keyence Corp. (Long Beach, Calif. 90802). Thirty-five grams of the 5:1 was poured onto the control mold in a plastic petri dish wrapped with aluminum foil. Five grams of the 20:1 was spun over the flow mold at 1,500 rpm for 60 sec on a Spincoater P6700 (Specialty Coating Systems, Indianapolis, Ind. 46278). Both were baked in an 80 deg C. oven for 30 min. The control layer was taken off its mold and cut into respective chip pieces. Control line ports were punched using a 20-gauge luer-stub adapter (Beckton-Dickinson, Franklin Lakes, N.J. 07417). Control layer pieces were washed with ethanol, blown dry with filtered air or nitrogen, and aligned on top of the flow layer under a stereoscope. The result was baked in an 80 deg C. oven for one hour. Chip pieces were then cut out and peeled off the flow layer mold. Flow line ports were punched with a 20-gauge luer-stub adapter. Chip pieces were washed in ethanol and blown dry before binding to the epoxide glass slides. The now assembled chips underwent final bake in an 80 deg C. oven overnight.

Sylgard PDMS elastomer was mixed with concentration (10:1), poured onto a silicon/photoresist mold, and used in a replication molding procedure. Once PDMS channels were completed, holes were mechanically punched to access the PDMS channels, and the elastomer was bonded to glass substrates at 80 C. Following this soft lithography procedure, the glass was covered with black electrical tape to avoid stray light penetration. The chip was ready to be used as described in U.S. Ser. No. 11/439,288 "High Throughput Multi-Antigen Microfluidic Fluorescence Immunoassays" filed on May 22, 2006 and incorporated herein by reference in its entirety.

Figure 4A:
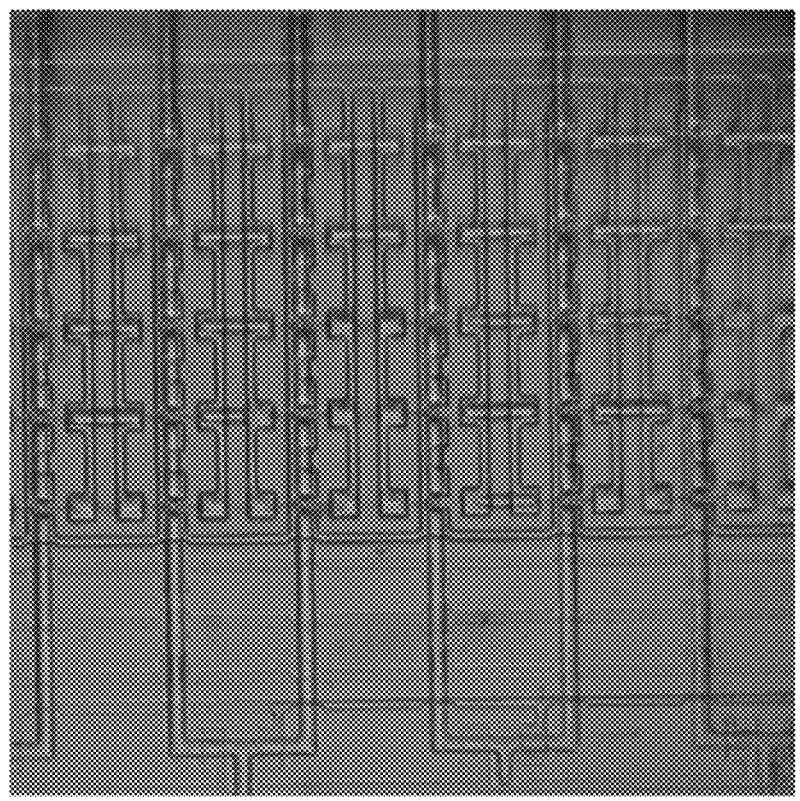
FIG. 4A shows a bottom view of a microfluidic chip
Figure 4B:
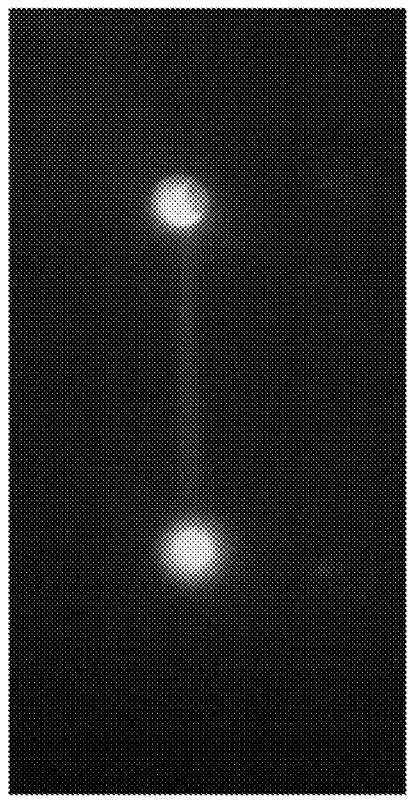
FIG. 4B shows a fluorescent image of a microchannel.

FIG. 4A and FIG. 4B show images taken with the arrangement shown in FIG. 1 and FIG. 2 following injection of a chip 10 with different concentration of the fluorophores Alexa Fluor 555 ranging from 0.01 to 300 g/ml in water. FIG. 4A shows a view of the microfluidic chip 10 with 100 micron wide fluid channels taken with only the emission filter 30 in place, in order to show the resolution of the device according to the present disclosure. FIG. 4B shows a 100 micron wide by 10 micron tall channel filled with Alexa Fluor 555 in a fluorescent image from the device according to the present disclosure.

The intensity in the resulting digital image matches the concentration of the Alexa dye—in the sense that only the fluorescent light 110 matching the filter 20 reaches the chip 120—and follows a non-linear relationship for higher dye concentrations as shown in the following FIG. 5, where the Alexa Fluor 555 dye emits at 555 nm once excited.

Figure 5:
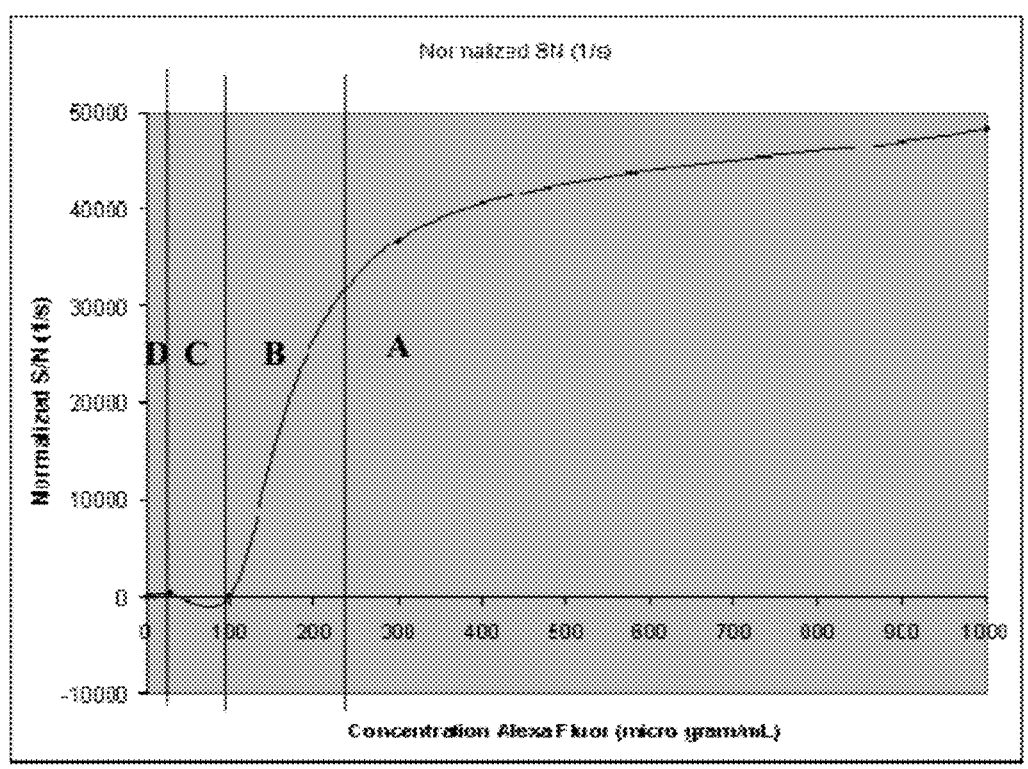
FIGS. 5-7 show graphs of concentration of Alexa Fluor with respect to normalized S/N.

In FIG. 5, signal to noise values of the fluorescence signal were normalized by applicants and plotted as a function of concentration. This number was found to generally increase with concentration when measuring the chip during UV lamp illumination. Above concentrations of 0.1 mg/ml, a linear relationship between fluorescence signal/noise and concentration is observed. At lower concentrations, the intensity/concentration graph reveals an anomalous peak in florescence intensity at 0.030 mg/ml. This peak, which indicates that the fluorescence drops with increasing dye concentration, can be explained by quenching mechanisms between dye molecules bonded to the surface of the flow channels and is also explained with reference to FIG. 6 and FIG. 7. If, instead of a mercury lamp, a LED (with a 2.5× larger intensity) at the desired excitation wavelength (xlamp 750 mW from cree) is employed as a fluorescence source, the SNR values are improved and the fluorophore is found to saturate.

As shown in FIG. 5, four interesting regions can be identified in the fluorescence SNR graph from highest concentration to lowest (right to left). In particular:

A—Saturation: At sufficiently high concentrations, saturation occurs in both the volume of the liquid and at the surface of the flow channels as the dye molecules are close enough to result in fluorescence quenching. Saturation on the surface results in significant fluorophore quenching as the fluorophores are very closely spaced. As the concentration of fluorophore is increased, non-specific sites can be driven towards fluorophore attachment. At even higher concentrations, the CMOS detector elements may saturate, leading to further nonlinearities in the fluorescence measurement. Moreover, at high concentrations, horizontal scattering of light out of the channel sides leads to a decrease in SNR.

B—First linear region: At lower concentrations, the CMOS detector array response becomes linear and volume quenching is largely avoided. However, surface Fluorescence Resonance Energy Transfer (FRET) energy transfer still occurs, but this term is expected to be linear with respect to concentration.

C—First rise in graph: Above a critical concentration, the fluorophore density in the volume is sufficiently high to ensure that the surface dye molecules are saturated and experience quenching. As the concentration decreases, fluorophores molecules are released from the surface layer and, as a result, dye molecules that were previously quenched now contribute to the fluorescence signal.

D—Second linear decrease: as the concentration is further decreased, the fluorescence signal from the liquid and the surface are linearly related as no quenching compromises the fluorescence signal. To avoid uncertainties with the nonlinear intensity behavior resulting from fluorescence quenching, it is possible to bleach the fluorophores. If the signal is reduced after optical irradiation, fluorophore concentrations are below the ones relevant for quenching. However, if the fluorescence intensity is increased, fluorescence quenching influences the signal. During optical irradiation, both free fluorophores contributing to the fluorescence signal as well as fluorophores that quench neighboring molecules are bleached. In most realistic clinical cases, surface treatments that decrease non-specific attachment to the surface and result in contributions from the surface will not be very important as the fluorescence dependence on concentration is linear for dilute concentrations. However, non-specific attachment to a surface can be characterized by observing the fluorescence quenching.

Filters for other wavelengths (HQ 605/75, HQ 610/75, HQ620/60) were also tested to obtain superior signal to noise values.

To improve the quality of the pictures and eliminate stray light, an opaque rectangular aperture can be placed above the chip 10. In particular, the dimensions of the aperture can be chosen to be slightly smaller than those of the PDMS chip, to ensure that only filtered light emission from the chip reaches the camera.

Digital images of the chip 10 can be taken, for example, at ISO settings of 100, 400 and 1600 and with shutter speeds ranging from 1/100 seconds to 2 seconds. Image analysis software (e.g., Astra Image 2.0 from Phase Space Technology) can be used to analyze these pictures. The measured red signal of the channel can be compared to the red signal from the background to evaluate the signal to noise using the above software. The following equation can be employed:

$$S/N = \frac{Red\_mean\_channel - Red\_mean\_background}{(Red\_deviation\_background)(Shutter\_speed)}$$

One of the advantages of conducting an antibody assay is the high specificity offered the antibodies bound to the epoxide surface, according to the epoxide chemistry to prepare the surface. After the analyte containing the antigen to be identified is flowed over that carefully prepared surface, the antigen is selectively removed from the flow and concentrated on the antibody-treated regions of the flow channels. Of course, the probability of binding can be increased by using microfluidic channels that pump the solution over the antibody-coated surface many times. It is important to ensure that many more binding sites are available than antigen molecules in the analyte, so that the fluorescence or absorption intensity can be quantitatively related to the antigen concentration. In a fluorescence immunoassay, the fluorescence intensity can be obtained with a digital image. With the appropriate selection of antibody chemistries deposited on the surface of an immunoassay chip, and after careful calibration to a develop a "standard curve" which gives signal intensity verses concentration for the system, a simple snapshot image suffices to provide analytical information, both qualitative and quantitative about many antigens within a fluidic specimen. The concentration obtained by the antibody surface treatment can lead to 1000× increases in the local concentration and thereby the fluorescence intensity of the surface compared with that of the liquid analyte.

In the table of FIG. 8, applicants have summarized some of the clinically relevant concentrations that need to be measured within blood samples for the particular application of cancer marker detection. As can be seen from the table of FIG. 8, concentrations ranging from the 10 pg/mL-150 mg/dL need to be measured, compared to 100 μg/mL minimum sensitivity demonstrated with our present digital camera instrument.

Therefore, antigens have to be concentrated significantly before such small concentrations can be measured, but this is enabled through microfluidic delivery of large volumes of sample over the functionalized surface. This observation renders the microfluidic immuno-assay approach much more sensitive than typical micro-array technologies, in which diffusion must take place before antigens can react with the functionalized surface. Thus, in micro-arrays, either much higher concentrations or longer times should be provided to obtain similar sensitivities limiting the use of simple digital cameras with limited signal to noise performance.

FIG. 8 also indicates the time required for a typical clinical analysis to be completed, and this ranges from several hours to several days. It is naturally desirable to reduce the time required to obtain test results and this is enabled through the use of inexpensive fluidics and imaging systems.

Applicants have shown that concentrations of 0.01-1000 mg/ml can be measured with a simple commodity off the shelf CCD camera well below the ranges needed for clinical evaluations of blood samples in microfluidic chips. When possibly combined with fluorescent assays and finger prick to plasma technologies this represents the core of a cheap, accessible medical testing. In particular, the components shown in FIG. 1 and FIG. 2 are all commodity off-the-shelf pieces, so that the sensitive immunoassay detector according to the present disclosure can be built for a few hundred dollars.

According to further embodiments, methods and devices, in particular microfluidic devices, for filtering fluids such as bodily fluids, are disclosed. Devices and components for filtering bodily fluids and in particular blood are known as such. Reference can be made, in particular, to U.S. Ser. No. 11/297,651, "Prototyping Methods and Devices for Microfluidic Components", filed on Dec. 7, 2005 and incorporated herein by reference in its entirety.

In the above application, the process of providing a "negative" mold, using wax, pouring a polymer on the mold to form the "positive" of the structure, and finally melting away the wax is described in detail. The final result of the process is a three-dimensional structure comprising interconnected microfluidic components comprising channels, vias and control sections.

The present disclosure provides a particular embodiment of a microfluidic filtering structure. More specifically, it provides a microfluidic blood filtering structure. In particular, the microfluidic filtering structure herein disclosed, comprises microfluidic channels which are completely sealed to a microfluidic filter, such that all fluid in the channel must pass through the filter. In particular, the micrifluidic channels size can is between 5 microns and 3 microns.

Figure 9A:
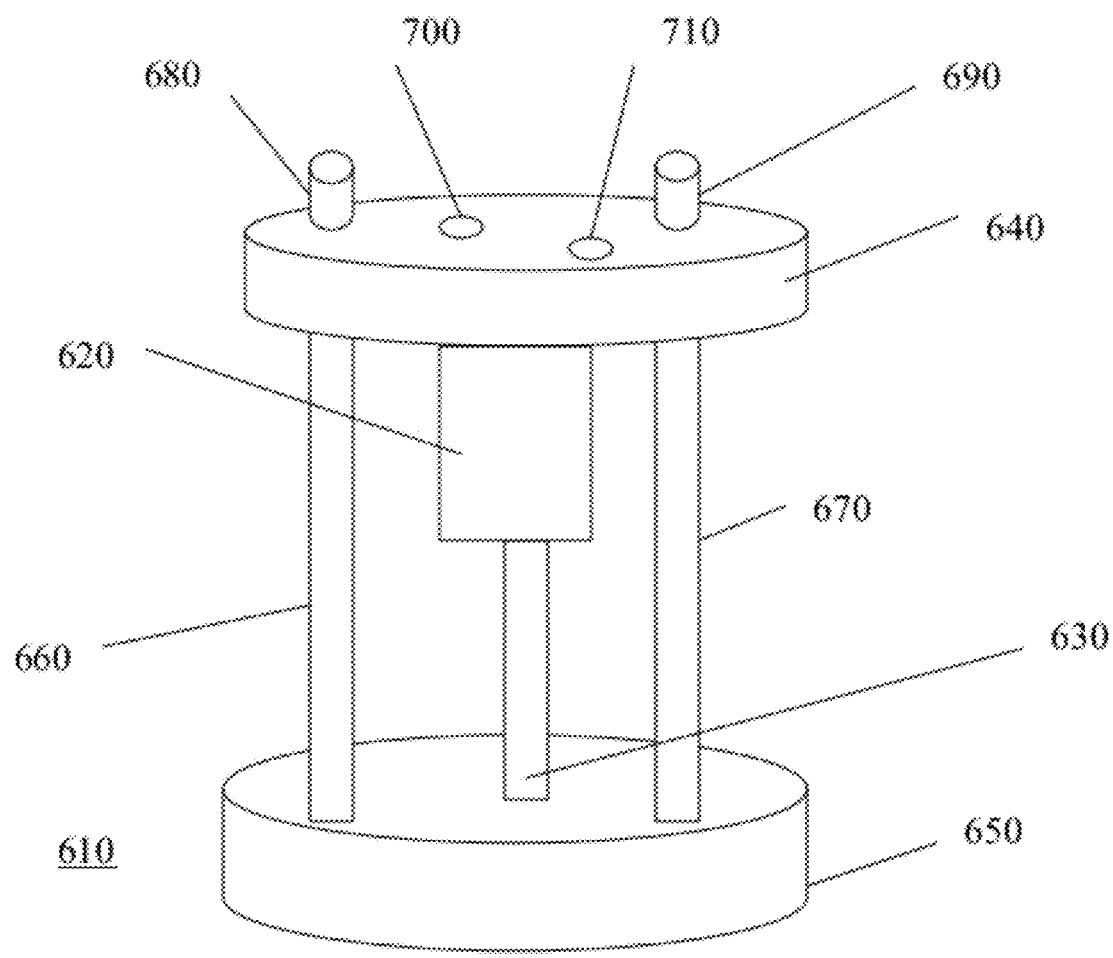
FIG. 9A shows a perspective view of a mold used to form the microfluidic blood filter in accordance with the present disclosure.

FIG. 9A shows a perspective view of the negative mold 610 used to form a microfluidic filtering device. The negative mold 610 can, for example, be made of aluminum.

The mold 610 comprises a first or top pin 620 and a second or bottom pin 630. The first pin 620 is a cylinder designed to mold the polymer (e.g., PDMS) such that the capillary tubes connecting to the microfluidic blood filter can be pushed in and sealed. The second pin 630 comprises a 24 gauge steel pin press fit into the aluminum in order to mold a hole during the casting process to allow a tight seal to standard 23 gauge pins typically used for microfluidics. The person skilled in the art will understand that diameters and materials can be changed according to the various uses.

The top pin 620 and bottom pin 630 are designed to be separated so that a piece of filter material (shown in a later figure) can be placed between them. The top pin 620 is connected to a top piece 640, while the bottom pin 630 is connected to a bottom piece 650. The top piece 640 and the bottom piece 650 are connected by screws 660, 670. The distance between top piece 640 and bottom piece 650 can be adjusted by means of bolts 680, 690. Adjustment of the distance allows the filter element to be compressed between the top piece 640 and the bottom piece 650. This ensures that a leak tight channel will be created in which blood must pass through the filter only. The top piece 640 also comprises holes 700, 710 that can be threaded and used to gently back the mold out of the polymer microfluidic structure when the casting process is finished.

Figure 9B:
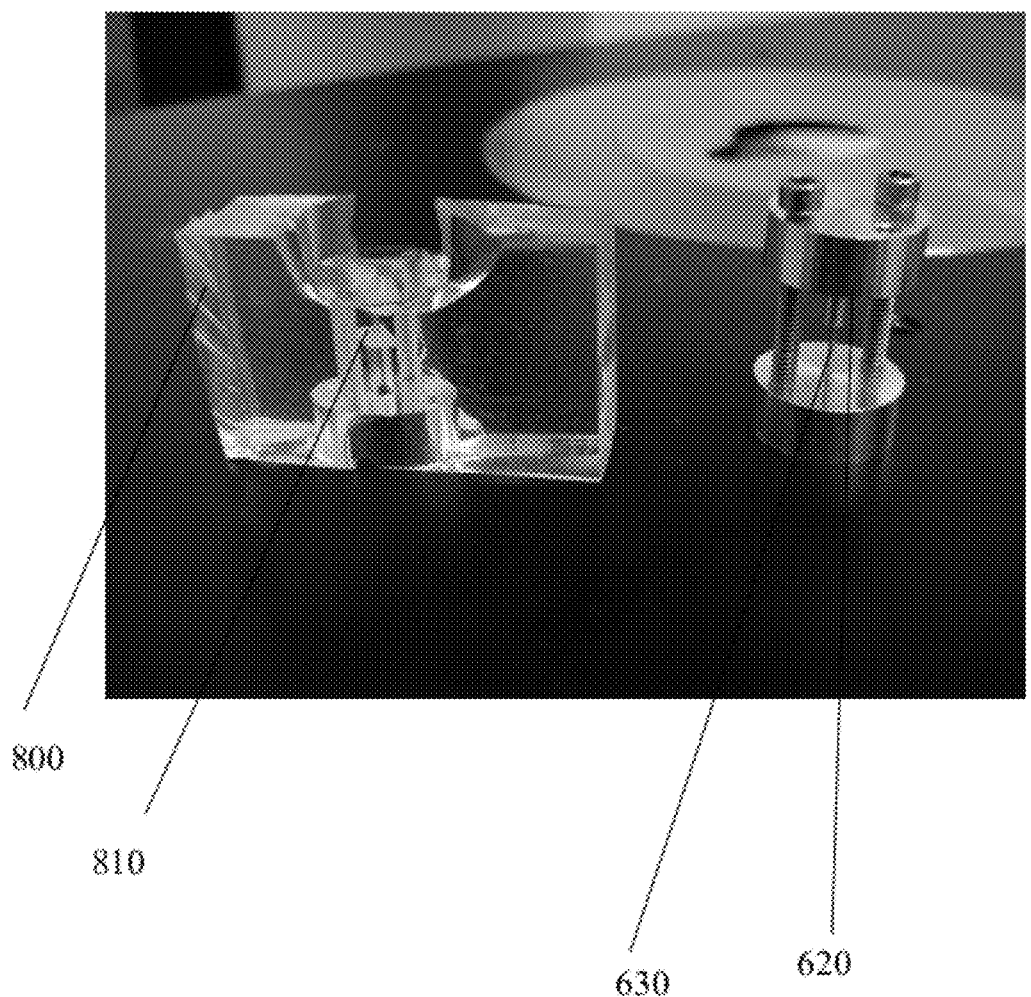
FIG. 9B shows a cast microfluidic polymer structure with an embedded filter element obtained through use of the mold of FIG. 9A in a casting process, together with the mold of FIG. 10.

FIG. 9B shows a cast microfluidic polymer structure with an embedded filter element obtained through use of the mold of FIG. 9A in a casting process such as the one described in U.S. Ser. No. 11/297,651.

In particular, a cast structure 800 is shown, which comprises the polymeric "positive" of mold 610 of FIG. 9A, together with an embedded filter element 810 located between the polymeric positive of top pin 620 and the polymeric positive of bottom pin 630, which constitutes the microfluidic channels in the structure.

During the process of fabrication to reach the structure of FIG. 9B starting from the mold of FIG. 9A, the filter paper 810 is placed between top pin 620 and bottom pin 630 and then bolts 680, 690 are used to squeeze and hold the filter paper in place. In an alternative embodiment the filter can be cast in a wax mold shaped like the metal mold of FIG. 9A with the filter trapped in the middle. A polymer such as PDMS or SIFEL® can be poured over the mold and cured, and then the wax melted out of the cured polymer, creating basically the same trapped filter and microfluidic channels in a monolithic polymer piece. At the end of the casting process, a monolithic three-dimensional PDMS device is obtained.

In certain embodiments a plurality of microfluidic filters is formed by multiple molds, such as the one described in FIG. 9A. In these embodiments, forming and releasing of the mold can be performed at the same time.

Figure 10:
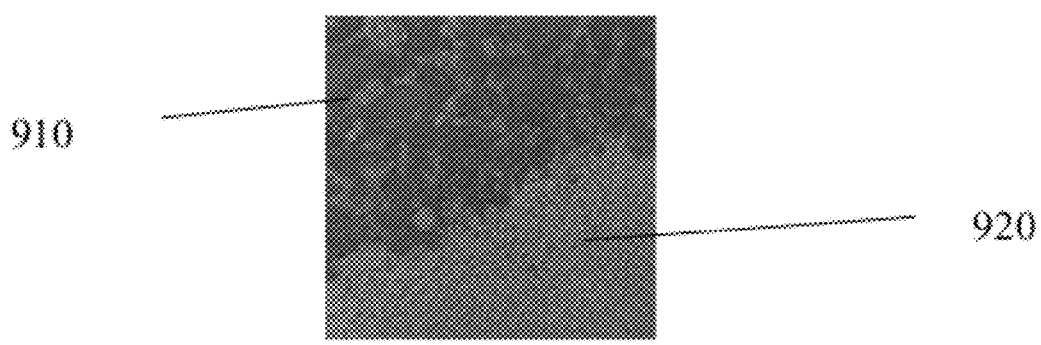
FIG. 10 shows a schematic view of an asymmetric porous membrane to be used as a blood filter for the present disclosure.

There are several commonly available filters, all of which are very cheap, especially in the small size needed for the device according to this disclosure. Applicants have chosen the BTS-SP series from Pall Corporation (East Hills, N.Y.). The BTS-SP medium features a highly asymmetric membrane that is specifically engineered for serum separation of whole blood, shown in the micrograph of FIG. 10. The graduated pore structure of the filter includes more open pores 910 on the upstream side and finer pores 920 on the downstream side. This high degree of asymmetry allows red and white blood cells to be captured in the larger pores while the plasma wicks into the smaller pores on the downstream side of the membrane. The large pore side of the medium serves as an absolute cell exclusion zone and performs very well in the device according to the present disclosure.

In some embodiment filtering can in principle include additional methods of purification or filtering, including but not limited to liquid chromatography, bead purification column, nanofabricated porous silicon membranes, or any other known method of purification or filtration (see e.g. Menake E. Piyasena, Tione Buranda, Yang Wu, Jinman Huang, Larry A. Sklar, and Gabriel P. Lopez* "Near-Simultaneous and Real-Time Detection of Multiple Analytes in Affinity Microcolumns" in Anal. Chem. 2004, 76, 6266-6273, and L. Hernandez1, M. Rudolph1, R. Lammertink2, J. Kornfield2, C. Zurital and F. A. Gomez1, Determination of Binding Constants of Polyethylene Glycol Vancomycin Derivatives to Peptide Ligands Using Affinity Capillary Electrophoresis in Chromatographia Volume 65, Numbers 5-6/March, 2007, both incorporated herein by reference in their entirety). A person skilled in the art, upon reading of the present disclosure, would be able to identify additional filtering system to be used in conjunction with assembly that will not be further discussed herein in details.

Figure 11:
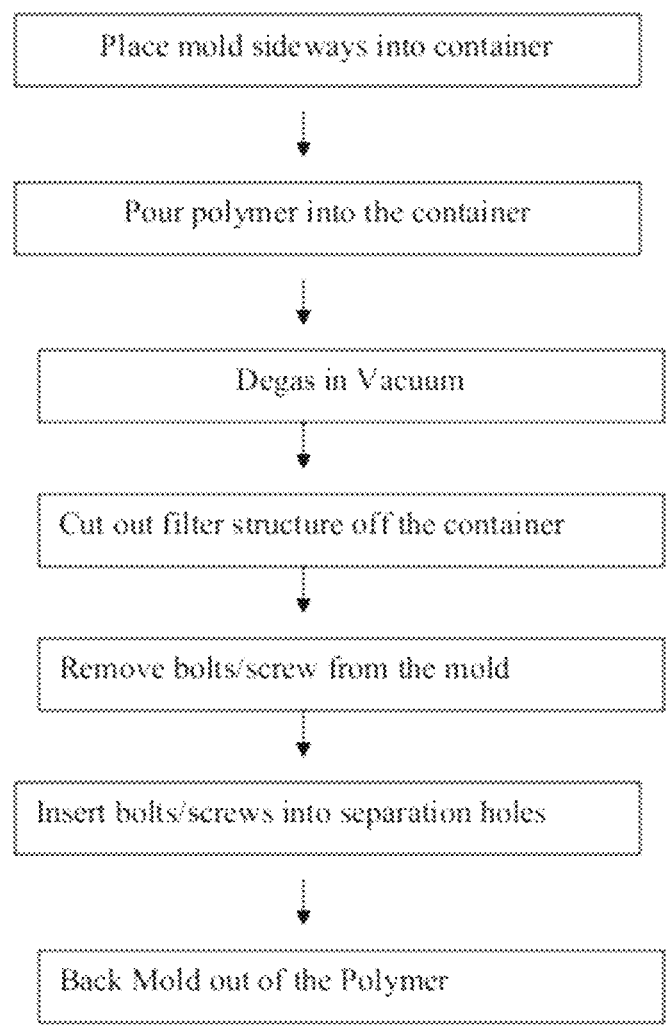
FIG. 11 shows a flow chart of the process to reach the structure of FIG. 11 starting from the mold of FIG. 10.

Turning back to the process of fabrication to reach the structure of FIG. 9B starting from the mold of FIG. 9A, when the mold 610 has been prepared, reference can be made to the flow chart shown in FIG. 11. The mold 610 is placed sideways into a standard container such as a Petri dish (step S1). A polymer, such as PDMS is then poured into the Petri dish (S2), and care is taken to completely cover the mold. The PDMS is mixed in a 10:1 ratio. After the mold is completely covered by the PDMS mixture, it is left to degas in vacuum (S3), until all air bubbles have been removed. At this point, the mold and the PDMS in the Petri dish are left to cure in an 80 degree Celsius oven for 1 hour (S4). After curing, the PDMS blood filter is cut out of the dish (S5) and the bolts and screws are removed from the mold (S6), freeing the two halfs. The bolts and screws are then inserted into the separation holes 700, 710 of FIG. 9A (step S7) and the mold is slowly backed out of the PDMS (S8). This process allows the blood filter paper 810 shown in FIG. 9B to remain intact in the PDMS filter.

In accordance with the present disclosure, the polymeric structure including the filter can further be provided, with at one end an inputting or receiving channeling structure, and on another end an outputting channeling structure.

In particular, the receiving channeling structure can be integrated with a capillary tube with an anti-coagulant (e.g., ethylene-diamine-tetra-acetic acid, (EDTA)) on it. In particular, the receiving end of the polymeric structure can be provided with capillaries of the type that are commonly used for finger stick blood draws and are available with a variety of anti-coagulants depending on the intended analysis to be performed. In some embodiments, anticoagulents can also be applied to the microfluidic channels formed by the polymeric positive of top pin 620 and bottom pin 630. Application can be performed for example via spray-dry coating or other method, such as evaporation of anticoagulant solutions in the microfluidic channels. As a consequence incoming blood can be anticoagulated in the microfluidic filter without relying on the capillary tube to add the anticoagulant.

The outputting other end of the blood filter, the end through which filtrate passes through, was made to interface with any standard microfluidic chip, e.g., through a 23 gauge pin. Whole blood would pass through the specially designed filter paper embedded in the PDMS blood filter, separating whole blood from the plasma, which would be used in the microfluidic chip.

The device according to the present disclosure can use the standard method of a finger stick blood draw using a capillary tube to provide the microfluidic circuit described above with blood plasma or serum that is ideally suited for downstream microfluidic evaluation.

The choice of the capillary tube to bring blood to the microfluidic filter in accordance with the present disclosure is specific to the test to be carried out on the blood because different anticoagulants are needed for different analyses. By way of example, the applicants have used the capillary tube StatSampler Capillary Blood Collectors from StatSpin (Iris Sample Processing, Westwood, Mass.) which has EDTA as an anti-coagulant to keep the blood sample from drying out or otherwise becoming unusable. These capillary tubes are used for example in doctor's offices as a standard finger prick blood draw and are available with several different anticoagulants. The person skilled in the art will understand that different capillary tubes and different anticoagulants can be used in conjunction with the microfluidic filter in accordance with the present disclosure.

In some embodiments the fluid is introduced through a pipe or a metal connector. In some embodiment the microfluidic channels can be coated with anticoagulant, for example by applying spray-dry method, or by filling the channel with an anticoagulant solution and allowing it evaporate (either naturally or by heating, or also by lyophilization)

Moreover, in the specific experiment conducted by applicants, a mouse blood sample from Bioreclamation Inc., already containing EDTA, was used, thus rendering the presence of an anticoagulant inside the capillary tube not necessary. In particular, 20 ml of mouse blood was stored and refrigerated at 4 degrees Celsius when not used, comprising two 10 ml samples, drawn a week from each other. The mouse blood was then drawn, 1 ml at a time, into a capillary tube. The capillary tube was then inserted into the upper portion of the filter.

In certain embodiments, the fluid can be drawn into the inputting microfluidic channel, either by capillary action or by vacuum and it is passed through the filter into the outputting microfluidic channel. In some of those embodiments, wherein a positive pressure is applied a cap can be applied to the inputting end of the microfluidic filtering device to seal it and apply pressure through the microfluidic channels the fluid is introduced into said microfluidic channels. In some of those embodiments the inputting end of the device/structure is shaped like a cone to ease introduction of the fluid.

Figure 12:
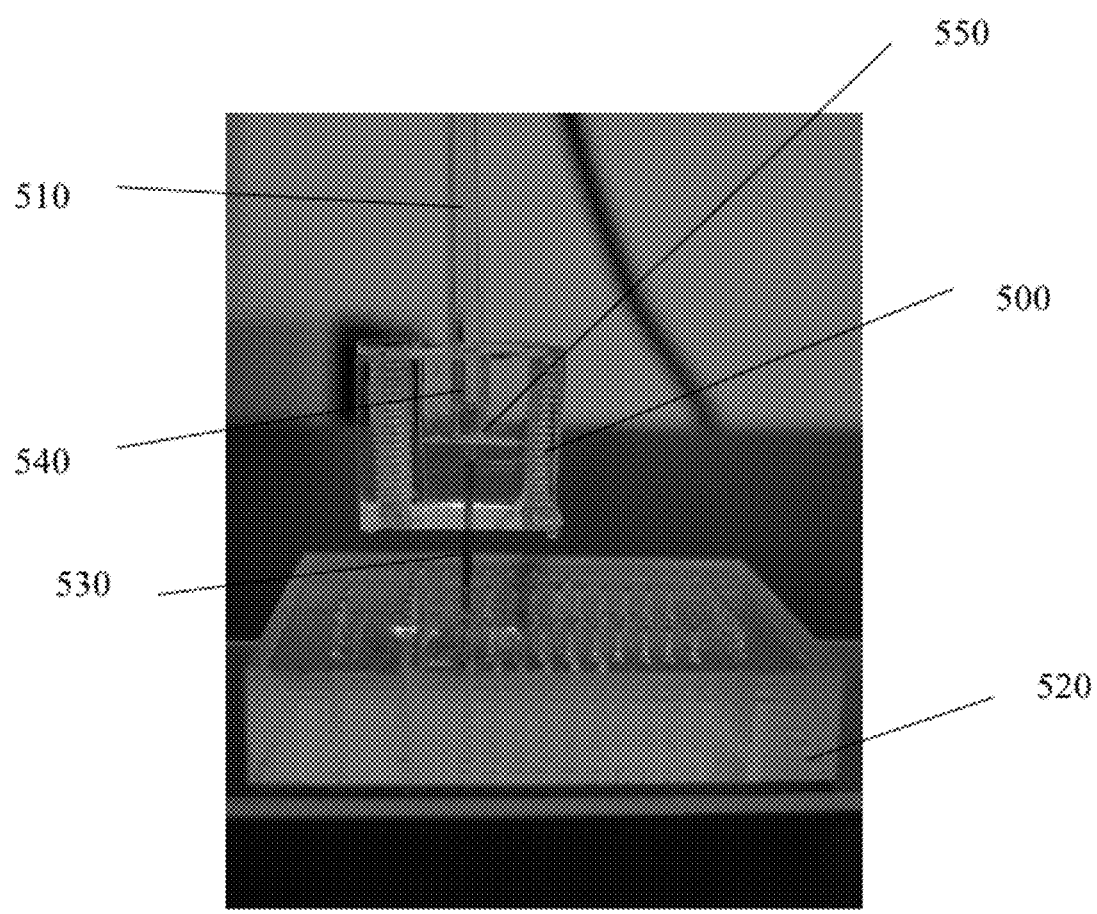
FIG. 12 shows a perspective view of the PDMS blood filter of the present disclosure integrated with a microfluidic blood analysis chip and a blood draw capillary tube.

FIG. 12 shows a perspective view of the PDMS blood filter of the present disclosure integrated with a microfluidic blood analysis chip and a blood draw capillary tube. In particular, the polymeric blood filtering structure 500 comprises a hollow cylinder 540 (which is a positive cast of the upper aluminum pin 620 of the mold 610) and a hollow pin 530 (which is a positive cast of the lower aluminum pin 630 of the mold 610), together with a blood filter 550 (e.g., the paper filter described in the example above). The filtering structure 500 is connected to a capillary tube 510 on it upper side and to a blood analysis microfluidic chip 520 on its lower side. It can be seen that the hollow pin 530 is connected to the blood filter 550 on its top side and to the microfluidic chip 520 on its bottom side.

Figure 13:
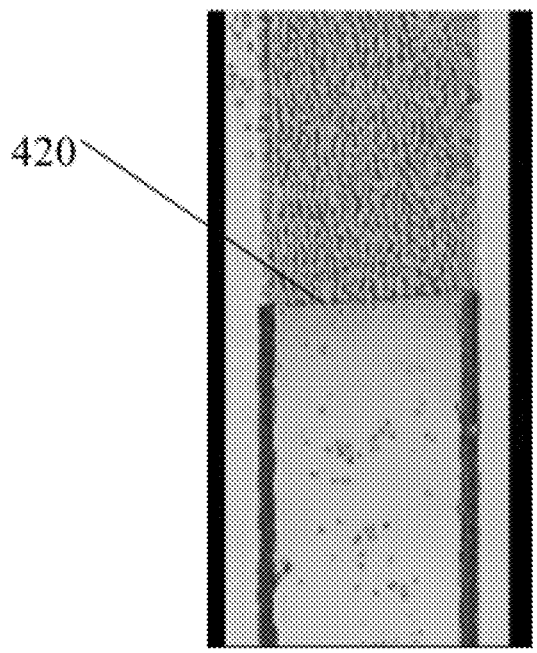
FIG. 13 shows a simulated side view of the blood filter device during operation.

The capillary tube 510 can be attached to a hose (not shown) supplied with dry nitrogen and the blood pumped through the filtering structure 500 at a constant pressure of 0.5 psi. This pressure is chosen by applicants for safety and to demonstrate that very little pressure is necessary to flow blood through the filter. The pressure by which blood is filtered can also be stabilized. Increasing the pressure from the above low level does serve to speed the blood flow. However, 1 ml of blood at a pressure of 0.5 psi went through the filtering structure 500 quickly. The filter 550 was shown to collect 80-100% of the available blood plasma which is typically half the total volume of the blood. 500 microliters of blood plasma is a very large amount of blood for most microfluidic applications which typically require nanoliters to microliters of fluid in order to perform analysis. A person skilled in the art would understand that additional pressure can be used as well as that a vacuum that can be applied to suck the fluid through the filter and the microfluidic chip FIG. 13 shows a simulated side view of the blood filter device during operation. The blood cells are all kept above the filter and plasma passes through below. In particular, the blood cells are stopped by filter material 420 and plasma continues to flow past the filter. One advantage of this design is that the same pressure or vacuum which pushes or pulls the blood through the filter can also be used to push the blood through the attached microfluidic chip 520 of FIG. 12.

Figure 14:
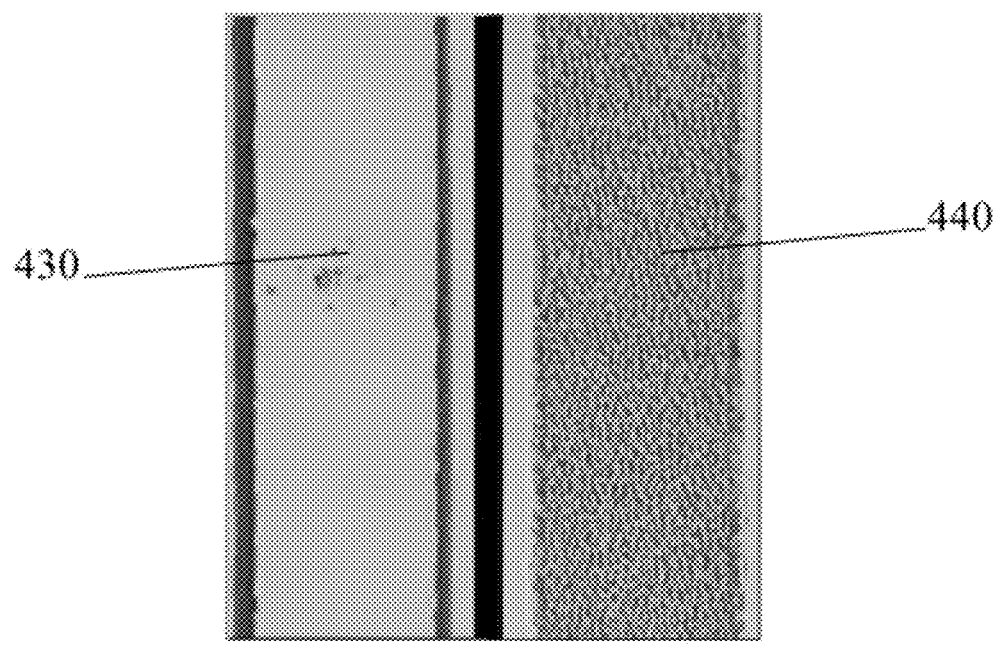
FIG. 14 shows two microfluidic channels, one with anti-coagulated mouse blood flowing through it and the other with the filter directly connected to its input port.

FIG. 14 shows two microfluidic channels, one with anti-coagulated mouse blood flowing through it and the other with the filter directly connected to its input port. In particular, both channels 430, 440 have dimensions of 100 micrometers in width, channel 430 with anti-coagulated mouse blood flowing through it and channel 440 with the filter directly connected to its input port. Channel 440 is full of blood cells, while channel 430 is clear and is flowing only plasma.

In summary, according to one of the aspects of the present disclosure, a PDMS microfluidic blood filter has been disclosed. The filter can be used with on-chip whole blood filtration for microfluidic blood analysis. The filter is able to filter the necessary volume of blood in an acceptable time frame. The PDMS blood filter can be used with standard microfluidic chips and is effective in separating plasma and blood cells from whole blood. The ability to collect whole blood from a simple finger prick and directly insert it into a microfluidic chip will allow blood analysis to be brought closer to the patient and eliminate the need for a painful venipuncture and a trained phlebotomist and simplify the collection and analysis of blood.

In some of the embodiments of the present disclosure, poly (dimethylsiloxane), or PDMS, was the material used for the blood filter, as it is more cheap and disposable, and has little affinity for proteins, RNA, DNA etc. The device can also be made from a variety of polymers including fluorinated Sifel and PFPE if the specific application requires the highest capture rate and sensitivy for rare species. PDMS is a good choice because it seals well to the filter, is compatible with traditional microfluidics and is flexible enough to seal to both the glass capillary tube and the standard metal pins used to introduce samples to microfluidic chips.

The fluorescence assay detector and the microfluidic filter device/polymeric structure, described above are combined in a microfluidic filtering and detecting system/assembly, which can be used for example for diagnostic purpose.

In the microfluidic assembly, the microfabricated filter can have any spatial orientation, including orientations that are sideways in the plane wherein the microfluidic chip is located.

In some embodiments, the microfabricated filter can be in principle produced, and desirably so, as a monolithic part of the microfluidic device itself, e.g. by being imbedded in the thick upper layer of the chip, during chip fabrication.

The system can also include a concentration stage/device whereby the fluid to be tested, for example urine, is processed through a capture system. The capture system can include but not limited to immunobeads or DNA hybridization beads, which would allow the processing of large quantities of sample for the detection of a molecule that, in view of the limited concentration in the fluid, would otherwise be difficult or impossible to handle in microfluidic devices within reasonable operation time scales (see e.g. Menake E. Piyasena, Tione Buranda, Yang Wu, Jinman Huang, Larry A. Sklar, and Gabriel P. Lopez* "Near-Simultaneous and Real-Time Detection of Multiple Analytes in Affinity Microcolumns" in Anal. Chem. 2004, 76, 6266-6273 incorporated by reference in its entirety).

In principle, the system may also include one or more additional subsystems/subassemblies e,g, for the performance of stages such as DNA sequencing PCR and/or RT-PCR in the sample (see e.g. Kartalov, Emil P. and Quake, Stephen R. (2004) Microfluidic device reads up to four consecutive base pairs in DNA sequencing-by-synthesis. Nucleic Acids Research, 32 (9). pp. 2873-2879, herein incorporated by reference in its entirety). In principle, the one or more subsystems can be operated in the assembly at a stage that precedes or follows the detection of the molecule of interest in the micro chips. A person skilled in the art, upon reading of the present disclosure will be able to identify those subsystems/subassemblies which will not be further described herein in details.

In certain embodiments, the microfluidic filtering and detecting assembly is arranged as a portable diagnostic system/assembly. In those embodiments, the diagnostic system/assembly comprises: a sample preparation stage/component: and a sample analysis stage/component, to detect analytes. The sample preparation stage/component can comprise a microfluidic circuit with a fluorescent fluid source, and the sample analysis stage/component can comprise: an excitation filter; an emission filter; a light emitting device to excite the fluorescent fluid source; and a detecting arrangement for detecting fluorescence images from the microfluidic circuit, with the microfluidic circuit located between the excitation filter and the emission filter.

In particular in the portable diagnostic system/assembly, the sample analysis stage is for the detection of important analytes at clinically relevant levels, wherein the detection is performed according to methods and devices apparent to the skilled person upon reading of the present disclosure. In an exemplary embodiment a portable fluorescence-immunoassay platform is used to measure many analytes on the same circuit at the same time, with indigenous sample preparation, and at clinically relevant levels.

In certain embodiments, a computer circuit is also included that controls a vacuum system (or positive pressure pump) to move the fluid, in particular plasma, through the filter and the chip in a controlled fashion. In some embodiments the computer also controls the LED, the detector, and gives feedback to patient and also to the doctor (e.g. via internet), stores data, gives patient history in graphs etc.

An advantage of the portable diagnostic system herein disclosed is that allows patients to obtain a diagnostic indication, by performing the following operations, introducing a microfluidic apparatus in the diagnostic assembly, or simply using another test in a multi use disposable chip, introducing the fluid to be tested, for example in case of blood analysis by puncturing a finger an place the finger over an inputting microchannel structure and reading the diagnostic indication provided, for example in a visual display.

In the following paragraphs, two different applications of the above discussed devices methods and systems will be shown. While the two applications below deal with the use of the system described above in small cell lung carcinoma and in multiple sclerosis, the person skilled in the art will understand that many other applications are possible.

A. Use in Small Cell Lung Carcinoma

In the following paragraphs, the application of a microfluidic fluorescent noncompetitive immunoassay system as the one described above will be discussed for the detection of the CRMP5 protein, a marker for SCLC (Small Cell Lung Carcinoma), and the miniaturization of the detector. Using monoclonal rat antibodies, an immunoassay stack specific to the CRMP5 marker was built and tested for specificity and sensitivity. A microfluidic filter device of the present application was used to able to separate serum from blood allowed for tests to examine marked blood. In particular, the filter device shown in FIG. 9B of the present application was used. A detector as shown in FIG. 2 of the present application, comprising an excitation and emission filter set, lens, LED, and CCD digital camera replaces bulkier optical microscope detectors and allows for images to be taken simultaneously off all chambers in the microfluidic device. By achieving appropriate signal to noise ratios with the miniaturized detector of FIG. 2 and using the immunoassay chip like the one described in U.S. Ser. No. 11/439,288 in tandem with microfluidic blood filters like the one described in FIG. 9B of the present application, the Applicants, approach cost efficient handheld devices capable of detecting SCLC with high specificity and sensitivity.

Using a two-layered PDMS chip for microfluidic fluorescence immunoassay as a platform (see, e.g. U.S. Ser. No. 11/439,288), Applicants investigate the creation of a point of care testing device capable of detecting the presence of the antigen CRMP5, a protein marker for small-cell lung carcinoma (SCLC) and in some cases thymoma. Applicants conducted a sandwich immunoassay test on a sample containing CRMP5 for proof of concept testing on the device's ability to detect a specific antigen. Collected data was analyzed for specificity and sensitivity. A miniaturized fluorescence detector was constructed from an inexpensive CCD camera, LED, lens and emission and excitation filter as shown in FIG. 2 above. A chip with fluorescence signal was observed through this system to show such a device was capable of simultaneously inspecting all chambers and still retain appropriate signal to noise ratio.

With the microfluidic chip sandwich (see element 10 of FIG. 2), immunoassays have been performed on a microscopic level and at antigen concentrations as low as 10 picoMolar and saturation concentrations in the 100 nanoMolar range. Here, Applicants conducted a proof of concept experiment; using the chip to detect the CRMP5 antigen, a marker of small-cell lung carcinoma, in the saturation range. In order to simplify the process fluorescently pre-tagged antibodies were used instead of biotinylation or tagged streptavidin. In order to investigate the practicality of a point-of-care testing apparatus constructed around such a platform, a portable and low cost detector like the one shown in FIG. 2 was developed and tested.

The materials and fabrication instructions for the manufacturing the chips can be seen, for example, in U.S. Ser. No. 11/439,288. The chip consisted of a control (top) layer and flow (lower) layer. The flow layer contained a 5 by 10 matrix of pathways 10 micrometer tall and 100 micrometer wide.

IgG rat monoclonal antibodies in ascites fluid were obtained from the Mayo Clinic in three variations. CR-1 binds to residues ~369-564 of CRMP-5, CR-3 binds to residues ~1-64, and CR-5 binds to residues ~57-376. CRMP-5 antigen, a 62 kilaDalton molecule, prepared from *E. Coli* in a 4.7 mg/mL concentration in dilute Phosphate Buffered Saline (PBS) was obtained from the Mayo Clinic.

Samples of each antibody were tagged with DyLight 547 using the Pierce Protein Labeling kit supplied by Pierce Biotechnology (Rockford, Ill., USA). The dye excites at 557 nm and emits at 570 nm.

PBS from Irvine Scientific (located Santa Ana, Calif., USA) and bovine serum albumin purchased from Sigma (St Louis, Mo., USA) were used to create the solution buffers. Tagged antibodies and the CRMP-5 antigen were reconstituted in PBS 0.1% BSA solution. Untagged antibodies were reconstituted in pure PBS 1× solution. Trishydroxymethylaminomethane (Tris Buffer) from Sigma-Aldrich (St. Louis, Mo., USA) was used as a flushing and pacifying agent.

An Olympus IX71 inverted microscope (Olympus America Inc. Melville, N.Y., USA) equipped with mercury lamp, Texas Red emission and excitation filter set (Absorption wavelength 595 nm, Emission wavelength 620 nm), and DFW −V500 Digital CCD cool charged-coupled device (CCD) from Sony served as the primary means of detection.

A miniaturized detector consisting of a 520 nm-535 nm (Green) Cree XLamp 3 7090 LED from ETG Corp (Los Angeles, Calif., USA) (see element 60 in FIG. 1 and FIG. 2), an emission and excitation filter set from Chroma (Excitation: HQ535/50x Emission: HQ610/75M; Rockingham, Vt., USA)—see elements 20 and 30 in FIG. 1 and FIG. 2—, and a Canon EOS digital Rebel camera (see element 50 in FIG. 1 and FIG. 2), was constructed and tested. Astra Image 2.0 software (Phase Space Technology) analyzed fluorescent signal captured from both systems.

Figure 15A:
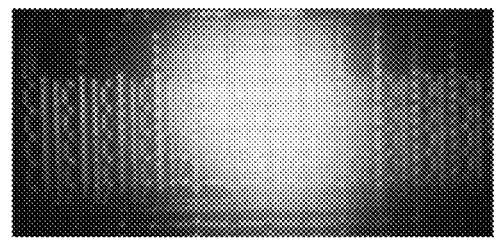
FIG. 15A shows an unfiltered image of a microfluidic chip taken with a miniaturized detector of the disclosure.
Figure 15B:
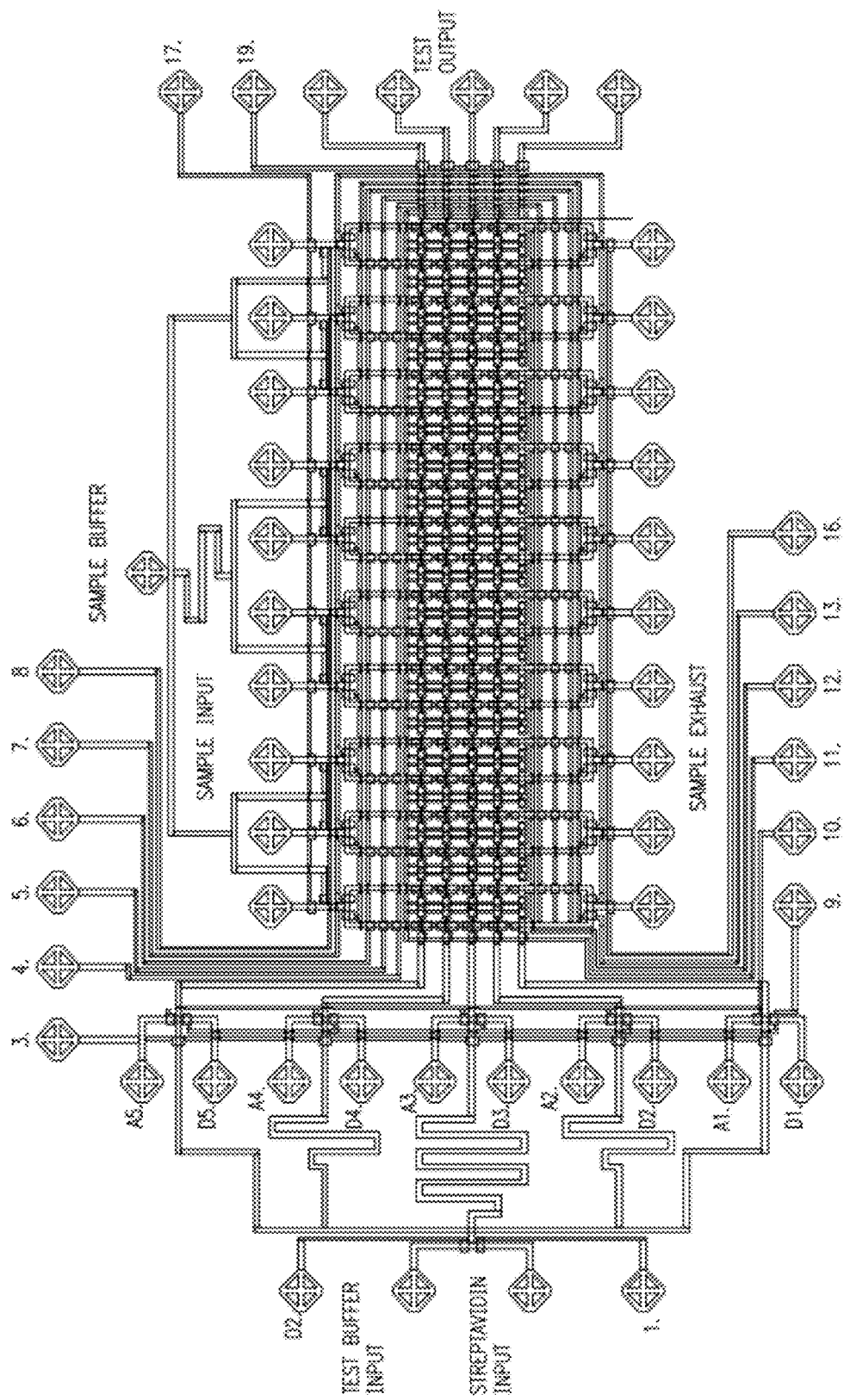
FIG. 15B shows a schematic diagram of a microfluidic chip suitable in the detector of the disclosure, wherein the control layer is shown in dark gray, and the flow layer is shown in light grey.

The microfluidic chip was mounted upon Super Epoxy SME glass slides from TeleChem International, Inc. (Sunnyvale, Calif., USA) as described in Kartalov et al. in Biotechniques 2006 number 1 volume 40, pp 85-90, herein incorporated by reference in its entirety. Applicants plugged 23 gauged tubes from New England Small Tubes (Litchfeld, N.H., USA) into the control and flow input ports and used. ID: 0.020 inch, OD: 0.060 inch Tygon Tubing from Cole-Parmer (Vernon Hills, Ill., USA) to connect the control channels to Lee-valve arrays (Fluidigm; San Francisco, Calif., USA) and the flow channels to the reagent supply. The related unfiltered image and schematic diagram of the microchip are shown in FIGS. 15A and 15B respectively.

Pressurized water filled the control layers until all air had diffused out of the channels. Applying pressure to any control input port via the software controlled valve arrays closed a microfluidic valve and shut off the flow in the corresponding reagent channel. Untagged monoclonal antibodies (CR5) were sent into the A5 input port and allowed to flow directly to the Test Output ports for several minutes. The horizontal flow channels were then flushed with Tris Buffer from the Test Buffer Input port to pacify any free epoxide locations and remove excess antibodies from the channel. Next, two samples were sent through the first and second Sample Input Ports. The first solution consisted of 5% CRMP5 by volume in a PBS 0.1% BSA mixture, the second a control contained only PBS 0.1% BSA. The vertical channels were filled and then circulated clockwise with a series of peristaltic pumps with a lap time of 20 seconds for 10 laps.

This process was repeated 10 times with the vertical channels being replenished after each cycle in order to ensure the antigens bonded to the antibody locations thoroughly. The vertical channels were then flushed with Tris Buffer from the Sample Buffer Input to the Sample Exhaust to remove the sample solutions. Fluorescently tagged monoclonal antibodies (CR1) were sent through the D5 input port and allowed to flow into the Test Output port for several minutes, completing the stack. Tris Buffer was sent through the Test Buffer Input to remove standing fluorescence.

The chip was placed upon the stage of the Olympus inverted microscope, excited by the mercury lamp, and examined through the Texas Red emission/excitation filter cube. Using a simple CCD camera images were taken using the microscope setup of the chambers containing both the antigen present sample and the control sample, and examined with Astra Image 2.0 software to determine the signal to noise ratio.

Figure 16A:
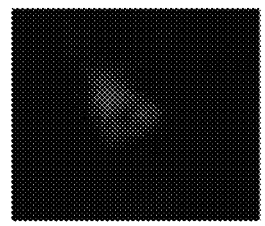
FIG. 16A shows an image illustrative of the signal from CRMP5 positive chambers viewed from a microscope
Figure 16B:
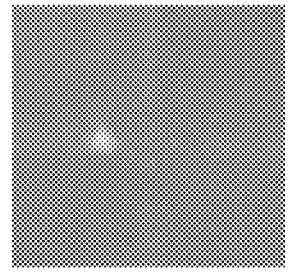
FIG. 16B shows a saturated fluorescent signal as observed with a miniaturized detector of the disclosure

In order to determine the quality of signal capture from the miniaturized detector in comparison to the bulkier microscope setup, a chip with a chamber of saturated signal was illuminated by the Green ETG LED through the HQ535/50x excitation filter and the signal captured by the EOS digital Rebel camera through the HQ610/75M emission filter. The image was likewise analyzed with the Astra Image 2.0 Software to determine the strength of the signal to noise ratio. The related signals as viewed from a microscope detector and from the detector of the present disclosure are shown in FIGS. 16A and 16B respectively.

Using the above mentioned experimental approach, the images of the CRMP5 present chamber and CRMP5 absent chambers were analyzed using Astra Image 2.0 software. The mean red signal of the chamber was compared with the mean red signal of the background. The signal to noise ration (SN) was determined by dividing the net signal by the standard deviation of the background noise. Using the microscope setup a SN of 107 was found from the CRMP5 positive chamber and a SN of 0.86 resulted from the CRMP5 negative chamber, showing a high level of specificity.

Results from the miniaturized detector proved practical though less proficient. Images taken from this portable setup of chambers saturated with fluorescence yielded a SN of 53.4. However the miniaturized detector proved capable of examining multiple chambers simultaneously and provided adequate qualitative data capable of differentiating between antigen present chambers and antigen absent chambers. Additionally the detector proved able to produce images of the chip with high clarity and good focus while requiring less space and costly materials than the microscope detection system.

In view of the above, Applicants have shown the ability to detect the CRMP5 antigen with the microfluidic fluorescent immunoassays. Furthermore the above test demonstrates that tagging antibodies directly with a protein dye proves as effective as attaching fluorescent streptavidin without the need for biotinylated antibodies and simplifying the immunoassay process. Due to time constraints and the shelf life of the proteins used, the sensitivity of the system with regards to CRMP5 has yet to be fully explored. Previous tests of the system with other antigens showed reliable detection as low as 10 pM.

B. Use in Multiple Sclerosis

The technology shown in the present application is also applicable for detection and diagnosis of multiple sclerosis (MS), a debilitating auto-immune disease. Applicants were able to demonstrate disease detection by identifying matrix metalloproteinase 9 (MMP-9), and GalC biomarkers for MS, in simulated patient serum. This is a proof-of-concept for the viability of a handheld multiple sclerosis attack early warning system. Such a detector could prove invaluable in the treatment of this disease. Multiple sclerosis is a disease that progresses through a series of exacerbations. If these exacerbations can be predicted through constant monitoring of blood species, treatments can be developed for use at the onset of MS attacks in order to minimize or eliminate the damage caused by the attack.

Multiple sclerosis is a debilitating auto-immune disease that affects the function of the central nervous system (CNS). An antibody response targets oligodendrocytes cells that are responsible for the myelination of neural axons. The immune response critically damages oligodendrocytes, halting production of myelin and leading to the rapid demyelination and eventual disintegration of the axons. Ultimately, the affected neurons lose the ability to conduct electrical impulses.

Figure 17:
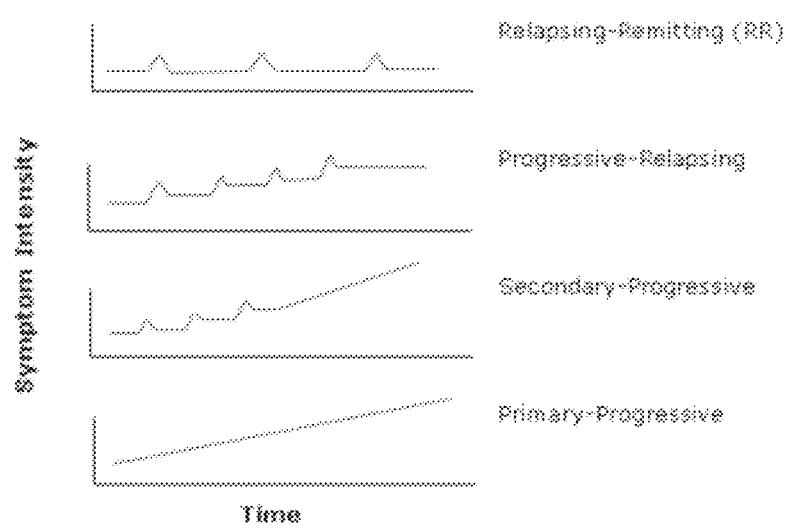
FIG. 17 shows graphs illustrating multiple sclerosis symptoms motifs.

Diagnosis of multiple sclerosis is done through characterization of the symptomatic response, which varies with each patient. More common symptoms, associated with the loss of neural function, include fatigue, numbness, spasticity, vision loss, and depression. Most patients fall into one of the four identified symptom motifs for multiple sclerosis: relapsing-remitting (RR), primary-progressive, secondary-progressive, and progressive relapsing. A graph illustrating multiple sclerosis symptoms motifs is shown in FIG. 17.

Approximately 85% of multiple sclerosis patients are initially diagnosed as relapsing-remitting; characteristics of these patients include episodes of acute symptoms followed by remissions of partial to complete recovery. Within ten years of the initial diagnosis about 50% of RR patients go on to exhibit secondary-progressive multiple sclerosis, which is characterized by a steady increase in symptom intensity with brief periods of acute symptoms and recovery. A smaller percentage of patients, diagnosed as primary-progressive, exhibit a steady increase in symptom intensity from the onset of the disease. However, a very small percentage of patients with multiple sclerosis demonstrate a progressive relapsing syndrome, wherein symptom intensity steadily increases along with intermittent periods of partial recovery.

Currently, there is no definitive serological test for multiple sclerosis. However, recent research has demonstrated the existence of specific biological markers for multiple sclerosis, which include matrix metalloproteinase 9 (MMP-9), a gelatinase enzyme that has the ability to cleave myelin, and Galactocerebroside (GalC), a transmembrane glycoprotein in oligodendrocyte cells that is a known target for demyelinating antibody responses. Furthermore, these markers have a demonstrated presence in the blood stream, making them promising candidates for immunological testing.

Figure 18:
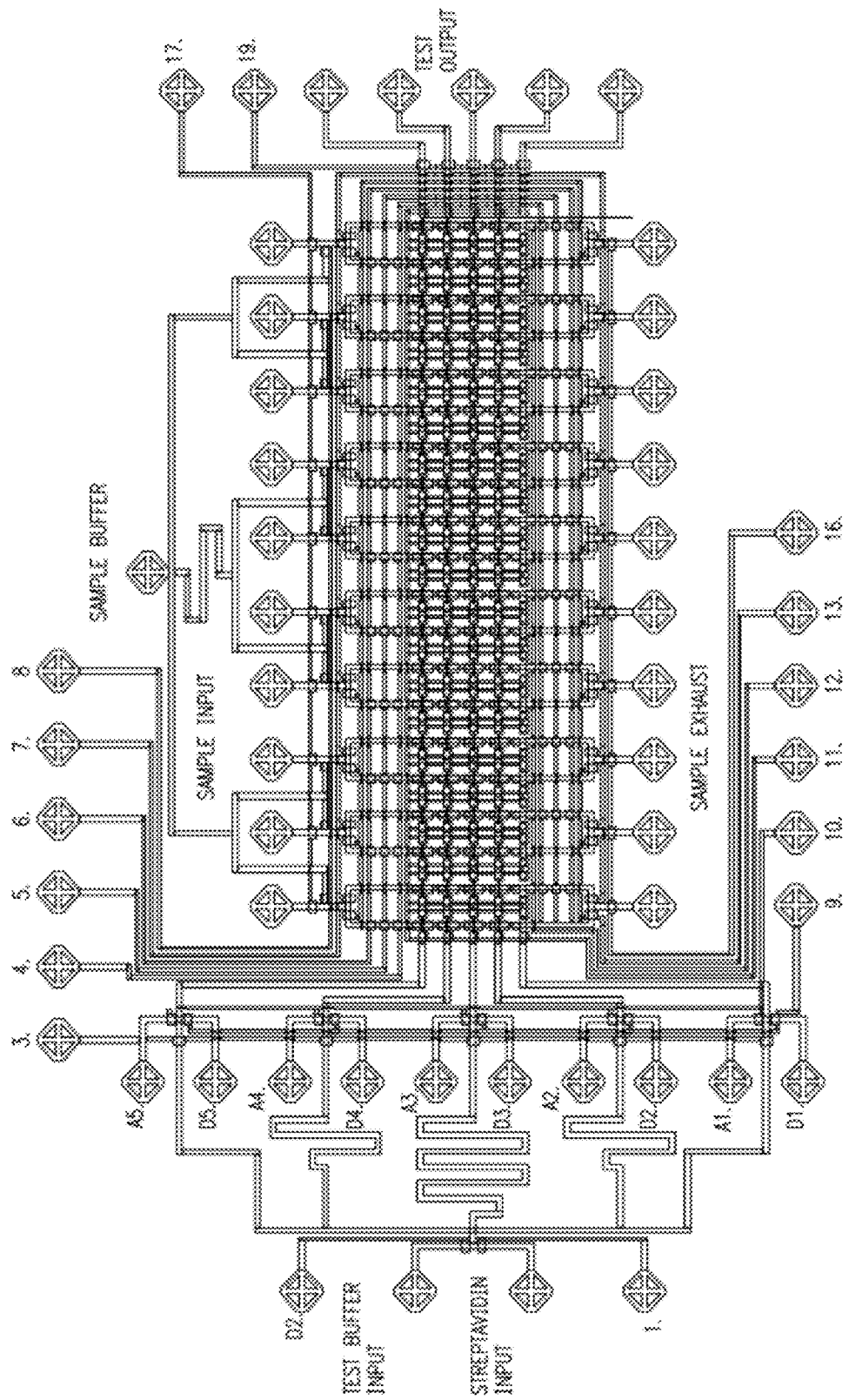
FIG. 18 shows a schematic diagram of a microfluidic chip suitable in the detector of the disclosure, wherein the control layer is shown in dark gray, and the flow layer is shown in light grey.
Figure 19:
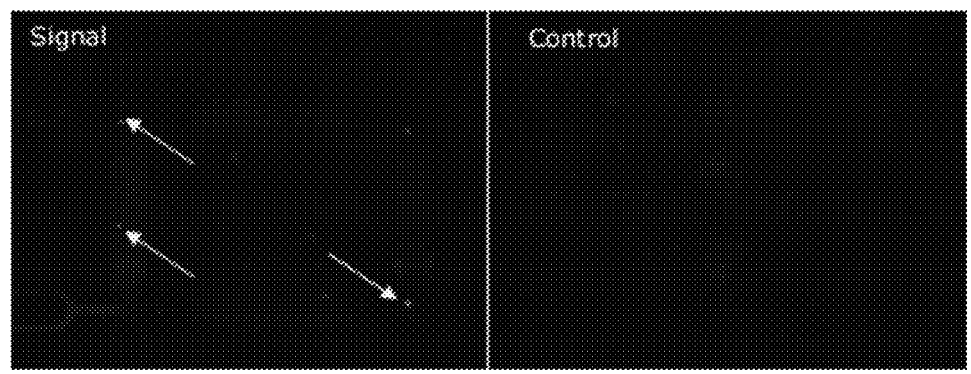
FIG. 19 shows the results of an MMP-9 Half Stack Immunoassay, wherein the left panel shows the signal from the immunoassay and the right panel shows the control experiment.

Applicants built a simple two-layer immunostack, using a high-throughput microfluidic immunoassay chip like the one described in U.S. Ser. No. 11/439,288 also schematically shown in FIG. 18, to illustrate a proof-of-concept of multiple sclerosis disease detection. A serum of MMP-9 was flowed through the coliseums of the fluidic chip and allowed to bond to free epoxide sites along the flow layer. Reference can be made, for example, to the microfluidic chip shown in FIG. 2 of U.S. Ser. No. 11/439,288. After passivating the remaining epoxide sites with TRIS buffer, fluorescently-tagged monoclonal anti-MMP-9 antibodies were pumped throughout the coliseums. Subsequently, the coliseums were flushed with TRIS buffer to liberate and remove and free-floating antibodies. Finally, the fluidic chip was illuminated with light of wavelength 547 nm, and the fluorescence emission was captured by a CCD. The results are shown in FIG. 19. Applicants inferred the presence of MMP-9 because of the luminescence of the fluorophores.

Figure 20:
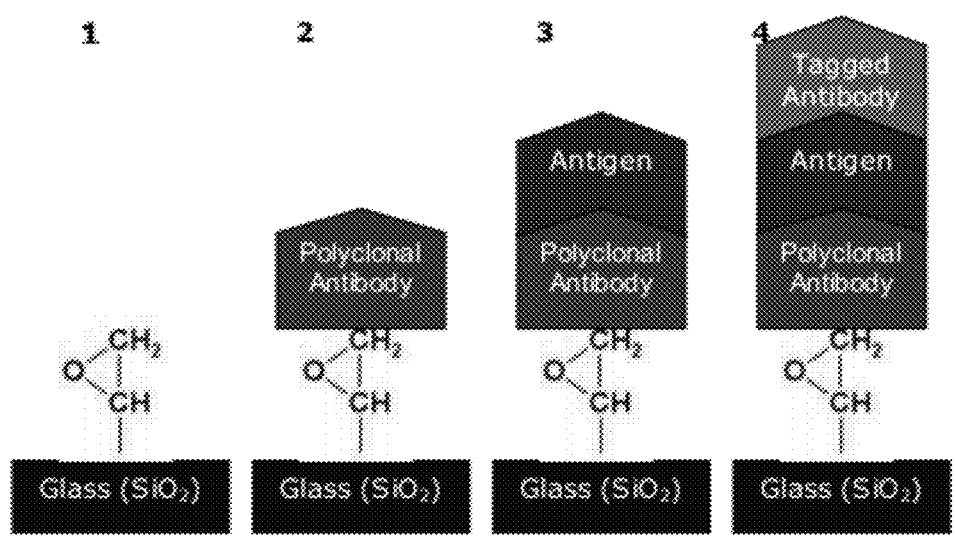
FIG. 20 shows a selective three-layer protein stack for MMP-9.
Figure 21:
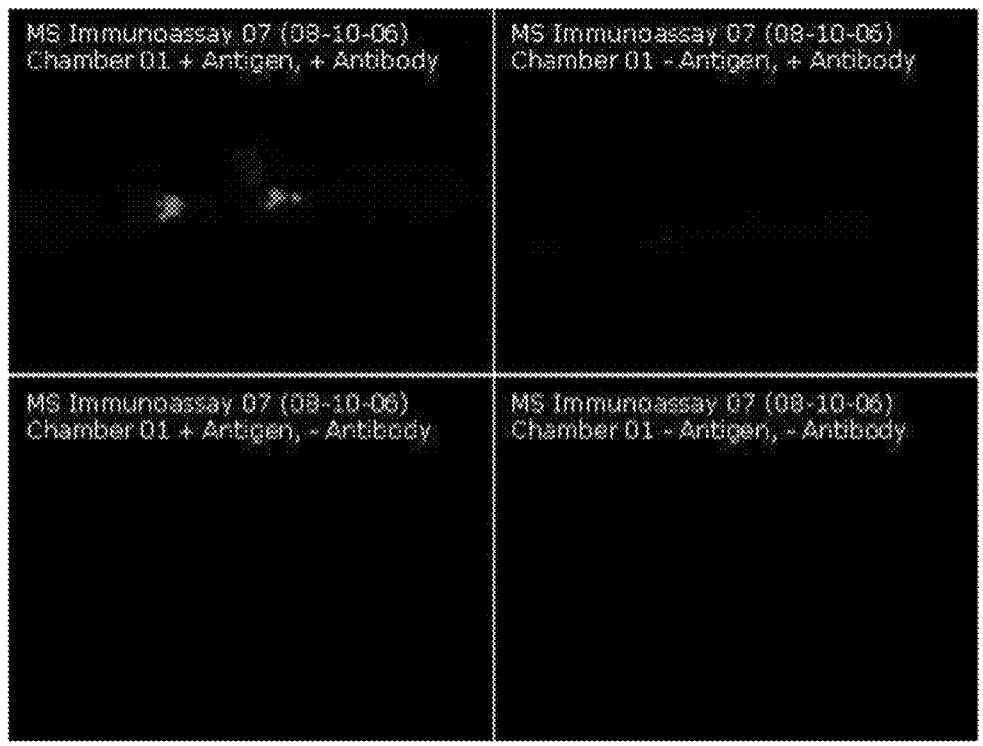
FIG. 21 shows a fluorescence image confirming presence of MMP-9.

Controlled detection of MMP-9 was done by fabricating a selective, three-layer protein stack (see FIG. 20) for MMP-9. First, polyclonal goat anti-human MMP-9 molecules were flowed through the coliseums and allowed to bond to the epoxide layer of the immunoassay chip. After passivating the remaining epoxide sides with TRIS buffer, simulated patient serum (consisting of a 470 nM solution of MMP-9) was flowed through the coliseums. The MMP-9 was immediately captured by the polyclonal anti-MMP-9 antibodies. Finally, fluorescently tagged monoclonal anti-MMP-9 antibodies were flowed through and mated with the MMP-9. Fluorescence imaging confirmed the presence of MMP-9 (see FIG. 21). Furthermore, fluorescence was observed only in coliseums which had exposure to MMP-9, validating the selectivity of the protein-stack.

Since only fully formed protein stacks have fluorescently tagged antibodies, the intensity of the fluorescence emission corresponds to the strength of the signal. In one assay, Applicants measured the red mean of the signal to be 227 with a standard deviation of 39.2. In comparison, the red mean of the noise was 9.224 with a standard deviation of 9.23. This resulted an SNR of 24 to 1. In another assay, Applicants observed a red mean of the signal to be 72.6 with a noise floor of 7.01, resulting in a SNR of 10 to 1. Successful immunoassays consistently had signal to noise ratios of 10 to 1 or greater.

In view of the above, Applicants demonstrated a proof-of-concept of multiple sclerosis disease detection through successful detection of the biomarker MMP-9. Furthermore, fluorescence detection of MMP-9 yielded SNR in excess of 24 to 1, with a minimum SNR of 10 to 1. Subsequent testing has suggested that MMP-9 antigen detection is possible with concentrations as low as 65 nM.

Figure 22:
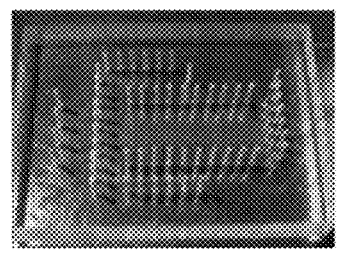
FIG. 22 shows a top view of a microfluidic chip suitable in the detector of the disclosure.

A high throughput immunoassay chip (see, e.g., element 10 in FIG. 1 and FIG. 2) was used to perform the microfluidic immunoassays. Soft lithography was used to fabricate the chips in polydimethylsiloxane (PDMS), an organic elastomer. The PDMS chips were then mounted and bonded on SuperEpoxy SME glass slides from TeleChem International. (see chip shown in FIG. 22)

The immunoassays were carried out using human MMP-3, MMP-9 antigens, anti-MMP-9 polyclonal antibodies, and monoclonal human anti-MMP-9 and anti-MMP-3 antibodies manufactured by R&D Systems. Subsequent immunoassays were performed with human GalC and anti-GalC antibodies provided by a collaborator.

The MMP proteins were reconstituted with TCNB buffer solution containing 50 mM Tris buffer, 10 mM $CaCl_2$, 150 mM NaCl, and Brij 35 (a stabilizing detergent manufactured by VWR Scientific.) The reconstituted proteins were aliquot into single-use centrifuged tubes, and refrigerated at −27° C. until needed. Furthermore, monoclonal human anti-MMP-9 and anti-MMP-3 were tagged with a Dylight 547 protein fluorescence labeling kit from the Pierce Corporation. The antibodies were stabilized with pure PBS buffer from Irvine Scientific.

The actual immunoassay was controlled with a Fluidigm BOB3 pressure-flow controller and was interfaced to the user with the Fluidigm uChip software. Antigen and antibody solutions were gently vortexed before input. Tris buffer was used to passivate epoxide groups in reagent channels. Excitation of the fluorophores was performed with a green light of 552 nm. Pictorial data was obtained using a Sony DFW-V500 Fire-i digital camera.

In summary, Applicants have developed an inexpensive and rapid read-out system for multi-antigen microfluidic fluorescence immunoassay systems. The fluidic analysis chips can be fabricated in polydimethylsiloxane PDMS, and have been shown to perform high throughput analysis on multiple analytes, with a measurement of over 100 fluorescent readings with sensitive detection down to 0.01 mg/ml concentrations.

Applicants have shown a device that will allow a patient to have an at home testing device for daily monitoring of blood protein levels. For instance, in multiple sclerosis it has been very difficult to detect the early stages of an attack in time to administer immunosuppressants in a timely manner in order to prevent nerve system damage. By using microfluidic technology combined with inexpensive CCD or other detectors it is possible to have an immunoassay chip as described in U.S. patent application Ser. No. 11/439,288 coupled with the CCD detector and appropriate electronics to monitor daily the levels of suspect proteins or other species in the blood, e.g. from a simple fingerprick that is passed through the chip. In this way the patient can be alerted when the proper marker protein rises so that he may alert his doctor and the appropriate action can be taken. Additionally, this chip can be used for researching and finding such marker by comparing daily protein levels with patient symptoms, outcomes and MRI scans.

Additionally, the above described system and method can be used for other types of diseases, such as a person with a known risk of cancer, or a patient who had hepatitis or some other known risk for certain types of cancer. Those persons can use a customized chip like the one described above to search daily for cancer markers circulating in the blood. In this way the patient can spot the tumor months earlier than it otherwise would have been detected and patient outcomes can be improved.

While several embodiments of the invention have been shown and described in the above description, numerous variations and alternative embodiments will occur to those skilled in the art. Such variations and alternative embodiments are contemplated, and can be made without departing from the scope of the invention as defined in the appended claims.

What is claimed is:

1. A microfluidic filtering device for filtering fluid comprising:
   a sealed, single-piece cast polymer structure made of transparent polymer material, the cast polymer structure having
      a vertical microfluidic inputting channel at one end of the cast polymer structure, into which fluid is adapted to be input,
      a vertical microfluidic outputting channel at another end of the cast polymer structure, from which filtered fluid is adapted to be output, and
      a filter element embedded within an internal empty space of the cast polymer structure, the filter element being located underneath the microfluidic inputting channel and above the microfluidic outputting channel,
   wherein the microfluidic inputting channel is axially aligned with the microfluidic outputting channel and the microfluidic outputting channel is adapted to be connected with a microfluidic circuit.

2. The microfluidic filtering device of claim 1, wherein the microfluidic channels are coated with an anticoagulant.

3. The microfluidic filtering device of claim 1, wherein the filter element is a paper filter.

4. The microfluidic filtering device of claim 1, wherein the filter is for serum separation of whole blood.

5. The microfluidic filtering device of claim 1, wherein the polymer is PDMS (Polydimethylsiloxane) or a fluorocarbon siloxane rubber composition.

6. The microfluidic filtering device of claim 1, wherein the cast polymer structure is formed from a mold, the mold comprising a separation space adapted to host the filter element when the cast polymer structure is formed from the mold.

7. The microfluidic filtering device of claim 6, the mold further comprising a top pin and a bottom pin at opposite ends of the separation space.

8. The microfluidic filtering device of claim 7, wherein the top pin of the mold is a cylinder-shaped pin.

9. The microfluidic filtering device of claim 6, wherein the separation space of the mold is an adjustable separation space.

10. The microfluidic filtering device of claim 7, wherein a distance between the top pin and the bottom pin of the mold is adjustable, to adjust the separation space.

11. The microfluidic filtering device of claim 6, the mold being a metal or wax mold.

12. The microfluidic filtering device of claim 7, wherein the bottom pin of the mold is connected with the top pin of the mold but separable from the top pin.

13. The microfluidic filtering device of claim 6, the mold further comprising a top piece connected with the top pin and a bottom piece connected with the bottom pin.

14. The microfluidic filtering device of claim 13, wherein the top piece of the mold comprises extraction holes.

15. The microfluidic filtering device of claim 1, wherein the microfluidic inputting and outputting channels each have a size between 3 microns and 5 microns.

16. The microfluidic filtering device of claim 1, wherein the diameter of the microfluidic inputting channel is larger than the diameter of the microfluidic outputting channel.

17. The microfluidic filtering device of claim 1, wherein the filter element is an asymmetric membrane having open pores on an upstream side and fine pores on a downstream side.

* * * * *